US007939710B1

(12) United States Patent
Apt et al.

(10) Patent No.: US 7,939,710 B1
(45) Date of Patent: May 10, 2011

(54) TROPHIC CONVERSION OF OBLIGATE PHOTOTROPHIC ALGAE THROUGH METABOLIC ENGINEERING

(75) Inventors: Kirk Emil Apt, Columbia, MD (US); F. C. Thomas Allnutt, Port Deposit, MD (US); David J. Kyle, Catonsville, MD (US); James Casey Lippmeier, Washington, DC (US)

(73) Assignee: Martek Biosciences Corporation, Columbia, MD (US)

( * ) Notice: Subject to any disclaimer, the term of this patent is extended or adjusted under 35 U.S.C. 154(b) by 3139 days.

(21) Appl. No.: 09/839,536

(22) Filed: Apr. 23, 2001

Related U.S. Application Data

(60) Provisional application No. 60/198,742, filed on Apr. 21, 2000.

(51) Int. Cl.
  *C12N 15/82* (2006.01)
(52) U.S. Cl. .......................... 800/278; 800/288; 800/290
(58) Field of Classification Search .................. 800/278, 800/288, 290
  See application file for complete search history.

(56) References Cited

U.S. PATENT DOCUMENTS

| | | | |
|---|---|---|---|
| 4,235,043 A * | 11/1980 | Harasawa et al. ................ | 47/1.4 |
| 4,857,467 A | 8/1989 | Sreekrishna et al. | |
| 5,100,792 A | 3/1992 | Sanford et al. | |
| 5,130,242 A | 7/1992 | Barclay | |
| 5,244,921 A | 9/1993 | Kyle et al. | |
| 5,374,657 A | 12/1994 | Kyle | |
| 5,397,591 A | 3/1995 | Kyle et al. | |
| 5,407,957 A | 4/1995 | Kyle et al. | |
| 5,492,938 A | 2/1996 | Kyle et al. | |
| 5,550,156 A | 8/1996 | Kyle | |
| 5,567,732 A | 10/1996 | Kyle et al. | |
| 5,658,767 A | 8/1997 | Kyle | |
| 5,661,017 A | 8/1997 | Dunahay et al. | |
| 5,711,983 A | 1/1998 | Kyle et al. | |
| 6,027,900 A | 2/2000 | Allnutt et al. | |
| 2008/0138851 A1 | 6/2008 | Apt et al. | |

FOREIGN PATENT DOCUMENTS

| | | |
|---|---|---|
| EP | 0108580 | 5/1984 |
| EP | 0 235 112 A2 | 9/1987 |
| JP | 3076583 | 4/1991 |
| WO | WO 93/05163 A1 | 3/1993 |
| WO | WO 94/20627 A1 | 9/1994 |
| WO | WO 96/31612 A2 | 10/1996 |
| WO | 9739106 | 10/1997 |

OTHER PUBLICATIONS

R. Lemoine et al., Identification of a pollen-specific sucrose transporter-like protein NtSUT3 from tobacco. FEBS Lett. 454 (1999), pp. 325-330.*
Apt et al., Mol Gen Genet. Oct. 16, 1996;252(5):572-9.Stable nuclear transformation of the diatom Phaeodactylum tricornutum.*
Asano et al., J Biol Chem. Dec. 25, 1991;266(36):24632-6. The role of N-glycosylation of GLUT1 for glucose transport activity.*
Gladue (1991) "Heterotrophic Microalgae Production: Potential for Application to Aquaculture Feeds, Rotifer and Microalgae Culture Systems." Proceedings of a U.S.—Asia Workshop, Honolulu, HI.
Gladue, R., "Heterotrophic Microalgae Production: Potential for Application to Aquaculture Feeds," *Rotifer and Microalgae Culture Systems, Proceedings of a U.S., Asia Workshop*, The Oceanic Institute, (1991).
Carić, J., et al., "Dietary effects of different feeds on the biochemical composition of the rotifer (*Brachionus plicatilis* Müller)," *Aquaculture*, 110; 141-150 (1993).
Watanabe, T., "Importance of Docosahexaenoic Acid in Marine Larval Fish," *J. World Aquacult Soc.*, 24; 152-161 (1993).
Apt, K.E., et al., "Commercial Developments in Microalgal Biotechnology," *J. Phycol.*, 35:215-226 (1999).
Chen, Feng, "High Cell Density Culture of Microalgae in Heterotrophic Growth," *TibTech*, 14:421-426 (1996).
Dunahay, Terri G., "Genetic Transformation of the Diatoms *Cyclotella cryptica* and *Navicula saprophila*," *J. Phycol.*, 31:1004-1012 (1995).
Fischer, Harald, et al., Targeting and Covalent Modification of Cell Wall and Membrane Proteins Heterologously Expressed in the Diatom *Cylindrotheca fusiformis* (Bacillariophyceae), *J. Phycol.*, 35:113-120 (1999).
Stevens, David R., "Genetic Engineering of Eukaryotic Algae: Progress and Prospects," *J. Phycol.*, 33:713-722 (1997).
Caspari, Thomas, et al., "Hexose/H+ Symporters in Lower and Higher Plants," *J. Exp. Biol.*, 196:483-491 (1994).
Amla, D.V., et al., "Metabolic Changes Associated with Cyanophage N-1 Infection of the Cyanobacterium *Nostoc Muscorum*," *Arch. Microbiol.*, 148:321-327 (1987)Beuf, Laurent, et al., "A Protein Involved-in Co-Ordiated Regulation of Inorganic Carbon and Glucose Metabolism in the Facultative Photoautotrophic Cyanobacterium *Synechocystis* PCC6803," *Plant Molecular Biology*, 25:855-864 (1994).
Charng, Yee-yung, et al., "Structure-Function Relationships of Cyanobacterial ADP-Glucose Pyrophosphorylase," *The Journal of Biological Chemistry*, 269(39):24107-24118 (1994).

(Continued)

*Primary Examiner* — Maria Leavitt
(74) *Attorney, Agent, or Firm* — Sterne, Kessler, Goldstein & Fox P.L.L.C.

(57) ABSTRACT

Most microalgae are obligate photoautotrophs and their growth is strictly dependent on the generation of photosynthetically-derived energy. In this study it is shown that the microalga *Phaeodactylurn tricornutum* can be engineered to import glucose and grow in the dark through the introduction of genes encoding glucose transporters. Both the human and *Chlorella kessleri* glucose transporters facilitated the uptake of glucose by *P. tricornutum*, allowing the cells to metabolize exogenous organic carbon and thrive, independent of light. This is the first successful trophic conversion of an obligate photoautotroph through metabolic engineering, and it demonstrates that methods of cell nourishment can be fundamentally altered with the introduction of a single gene. Since strains transformed with the glucose transport genes are able to grow non-photosynthetically, they can be exploited for the analysis of photosynthetic processes through mutant generation and characterization. Finally, this work also represents critical progress toward large-scale commercial exploitation of obligate phototrophic algae through the use of microbial fermentation technology, eliminating significant limitations resulting from light-dependent growth.

6 Claims, 6 Drawing Sheets

OTHER PUBLICATIONS

Dunahay, Terri G., et al., "Genetic Engineering of Microalgae for Fuel Production," *Applied Biochemistry and Biotechnology*, 34/35:331-339 (1992).

Hallmann, Armin, et al., "The Chlorella Hexose/H+ Symporter is a Useful Selectable Marker and Biochemical Reagent When Expressed in *Volvox,*" *Proc. Natl. Acad. Sci. USA*, 93:669-673 (1996). .

Caceres, Odecio, "Some Features on the Growth of Microcystis Aeruginosa Kuetz, Emend, Elenkin in ASM- Medium," *Rev. Microbiol.*, Sao Paulo, 19(3):223-228 (1988).

Matsuoka, Makoto, et al., "Expression of Photosynthetic Genes from the $C_4$ Plant, Maize, in Tobacco," *Mol. Gen. Genet.*, 225:411-419 (1991).

Walmsley, A.R., et al., "Sugar Transporters from bacteria, Parasites and Mammals: Structure-Activity Relationships," *Trends Biochem. Sci.*, 23(12):476-481 (1998). Abstract Only.

Barrett, M.P., et al., "Trypanosome Glucose Transporters," *Mol. Biochem. Parasitol*, 91(1):195-205 (1998). Abstract Only.

Mueckler, M., et al., "Sequence and Structure of a Human Glucose Transporter," *Science*, 6:941-945 (1985).

Milbrandt, B., et al., "Glucose-Transport-Deficient Mutants of Schizosaccharomyces Pombe: Phenotype, Genetics and Use for Genetic Complementation," *Microbiology*, 140:2617-2623 (1994). Abstract Only.

Henderson, P.J., "The Homologous Glucose Transport Proteins of Prokaryotes and Eukaryotes," *Res. Microbiol.*, 141(3):316-328 (1990). Abstract Only.

Kruckeberg, A.L., "The Hexose Transporter Family of *Saccharomyces cerevisiae,*" *Arch. Microbiol.*, 166(5):283-292 (1996). Abstract Only.

Bisson, L.F. et al., "Yeast Sugar Transporters," *Crit. Rev. Biochem. Mol. Biol.*, 28(4):259-308, (1993). Abstract Only.

Apt. K. E., et al., Stable Nuclear Transformation of the Diatom *Phaeodactylum Tricornutum, Mol. Gen. Genet.*, 252:572-579 (1996).

Cossar, J.D., "Thioredoxin as a Modulator of Glucose-6-Phosphate Dehydrogenase in a N2-Fixing Cyanobacterium," *Journal of General Microbiology*, 130:991-998 (1984).

Charng, Yee-yung, "Mutagenesis of an Amino Acid Residue in the Activator-Binding Site of Cyanobacterial ADP-Glucose Pyrophosphorylase Causes Alteration in Activator Specificity," *Archives of Biochemistry and Biophysics*,318(2):476-480 (1995).

Stevens, D.R., et al., Development of a Dominant Selectable Marker for Nuclear Transpormation of *Chlamydomonas reinhardtii, Journal of Experimental Botany*, 46:37 (1995).

Broedel, Sheldon E., "Growth-Phase-Dependent Induction of 6-Phosphogluconate Dehydrogenase and Glucose 6-Phosphate Dehydrogenase in the *Cyanobacterium Synechococcus* sp. PCC7942," *Gene*, 109:71-70 (1991).

Adhikary, S.P., "Utilization of Organic Substrates by Two Filamentous Cyanobacteria Under Various Growth Conditions," *Acta. Microbiologica Hundarica*, 35:101-106 (1988).

Droop, M.R., "Heterotrophy of Carbon," in *Algal Physiology and Biochemistry*, Stewart, W.D.P., ed., University of California Press, Berkeley, CA USA, pp. 530-559 (1974).

Hellebust, J.A. and Lewin, J., "Heterotrophic Nutrition," in *The Biology of Diatoms*, Werner, D., ed. University of California Press, Berkeley, CA USA, pp. 169-197 (1977).

Hu, D., et al., "The *C. reinhardtii* $CF_1$ with the mutation βT168S has high ATPase activity," *FEBS Letters 421*:65-68, Federation of European Biochemical Societies, London, UK (1998).

Kröger, N., "The Sweetness of Diatom Molecular Engineering," *J. Phycol. 37*:657-658, The Phycological Society of America, San Marcos, CA (2001).

Lewin, J. and Hellebust, J.A., "Utilization of Glutamate and Glucose for Heterotrophic Growth by the Marine Pennate Diatom *Nitzschia laevis,*" *Marine Biology 47*:1-7, Springer-Verlag, New York, NY USA (1978).

Starr, R.C. and Jaenicke, L., "Purification and Characterization of the Hormone Initiating Sexual Morphogenesis in *Volvox carteri* f. *nagariensis* Iyengar," *Proc. Nat. Acad. Sci. USA 71*:1050-1054, National Academy of Sciences, Washington, DC USA (1974).

Vazhappilly, R. and Chen, F., "Eicosapentaenoic Acid and Docosahexaenoic Acid Production Potential of Microalgae and Their Heterotrophic Growth," *JAOCS 75*:393-397, AOCS Press, Urbana, IL USA (1998).

Zaslavskaia, L.A., et al., "Transformation of the Diatom *Phaeodactylum tricornutum* (Bacillariophyceae) With a Variety of Selectable Marker and Reporter Genes," *J. Phycol. 36*:379-386, The Phycological Society of America, San Marcos, CA USA (2000).

Zaslavskaia, L.A., et al., "Trophic Conversion of an Obligate Photoautotrophic Organism Through Metabolic Engineering," *Science 292*:2073-2075, American Association for the Advancement of Science, Washington, DC USA (2001).

European Search Report for Application No. EP 06 01 9651, completed on Mar. 21, 2007, European Patent Office, Munich, Germany.

International Search Report for International Application No. PCT/US01/12789, dated Jan. 15, 2002, European Patent Office, Rijswijk, The Netherlands.

\* cited by examiner

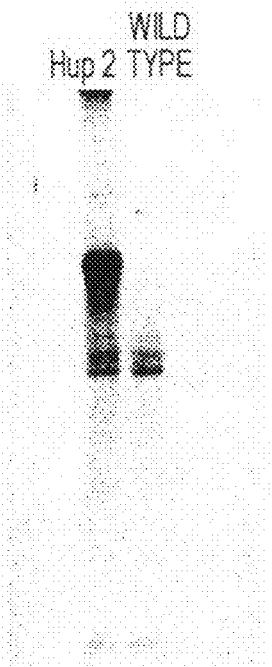
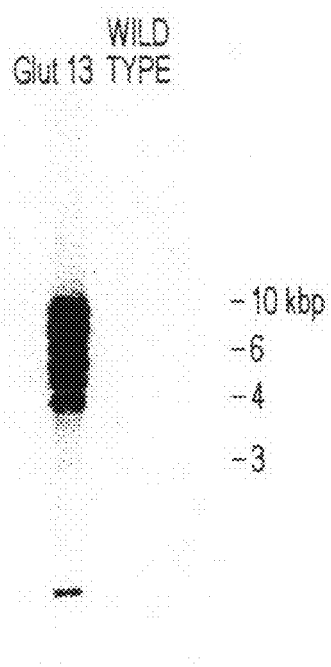
FIG. 2A  FIG. 2B
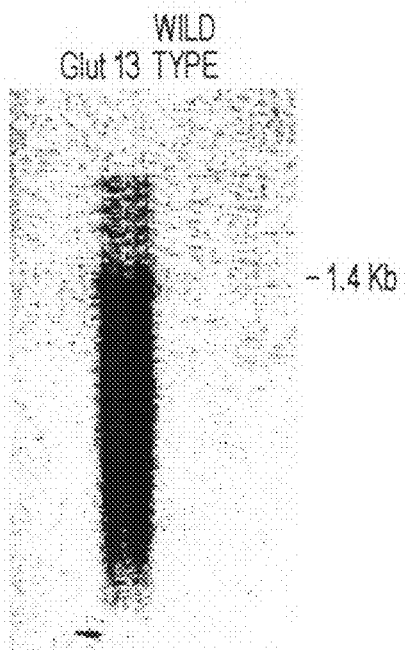
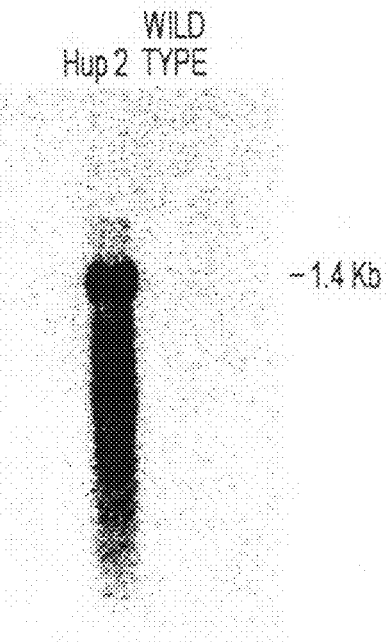
FIG. 3A  FIG. 3B

TROPHIC CONVERSION OF OBLIGATE PHOTOTROPHIC ALGAE THROUGH METABOLIC ENGINEERING

This application is based on U.S. provisional application No. 60/198,742, filed Apr. 21, 2000, which is incorporated herein in its entirety.

This work was supported by National Science Foundation Small Business Innovation Research Grant #9710990. The U.S. Government may have certain rights in this invention.

REFERENCE TO SEQUENCE LISTING SUBMITTED ELECTRONICALLY

The content of the electronically submitted sequence listing (Name: 09 839536.txt; Size: 1,803 bytes; and Date of Creation: Oct. 22, 2010) filed herewith is incorporated herein by reference in its entirety.

BACKGROUND

1. Field of the Invention

This invention is directed to methods for genetic transformation of algae, and in particular to conversion of obligate phototrophic organisms to recombinant organisms capable of heterotrophic growth.

2. Review of Related Art

Photosynthetic algae are the primary producers in aquatic environments, accounting for a significant proportion of worldwide $O_2$ production and $CO_2$ fixation in aquatic environments. Tréquer, P., Nelson, D. M., Van Bennekom, A. J., DeMaster, D. J., Leynaert, A. & Quéquiner, B. 1995. "The silica balance in the world ocean: a reestimate," *Science* 269: 375-79. Algae-are also needed for aquaculture and are used to produce many valuable products. For example, algae are used for the production of pigments (e.g., β-carotene, phycobiliproteins), oils with nutritional value (e.g., docosahexaenoic acid), and stable isotope-labeled biochemicals (e.g., $^{13}C$-glucose). Algae are also used as food for human and animal consumption.

In general, algae require light to drive photosynthesis for the production of the chemical energy required for cellular metabolism. Many are obligate phototrophs, meaning they have an absolute requirement for light to survive. Droop M R "Heterotrophy of Carbon." in *Algal Physiology and Biochemistry, Botanical Monographs,* 10: 530-559, ed. Stewart W D P, University of California Press, Berkeley (1974). Such algae are unable to utilize exogenous organic compounds (such as glucose, acetate, etc.) as an energy or carbon source. Some algae are able to utilize either internal or external fixed carbon. A small number of algae are obligate heterotrophs: they are incapable of photosynthesis, relying entirely on exogenous organic compounds as energy and carbon sources.

Large scale cultivation of photosynthetic algae requires a relatively controlled environment with a large input of light energy. The requirement for light and the high extinction coefficient of chlorophyll in these organisms has necessitated the design and development of novel systems for cultivation and large scale growth. Chaumont, D. 1993. "Biotechnology of algal biomass production: a review of systems for outdoor mass culture." *J. Appl. Phycol.* 5:593-604. A common limitation to all of these systems is the need to supply light to the culture, making it advantageous to maximize the surface-to-volume ratio of the culture. As cell densities increase, self shading becomes a limiting factor of productivity, resulting in relatively low biomass levels.

Most commercial production techniques use large open ponds, taking advantage of natural sunlight, which is free. These systems have a relatively low surface area to volume ratio with corresponding low cell densities. It is also very difficult to exclude contaminating organisms in an open pond. This difficulty restricts the usefulness of open ponds to a limited number of algae that thrive in conditions not suitable for the growth of most organisms. For example, *Dunaliella salina* can be grown at very high salinities. Apt K E et al, "Commercial Developments in Microalgal Biotechnology," *J Phycol.* 35:215-226 (1999).

Enclosed photobioreactors, such as tubular photobioreactors, are an alternative outdoor closed culture technology that utilize transparent tubes enclosing the culture minimizing contamination. They provide a very high surface to volume ratio, so cell densities are often much higher than those that can be achieved in a pond. However, even in technologically advanced photobioreactors, the maximum algal cell densities attained are relatively low. In both ponds and bioreactors, low densities necessitate large volume cultures, which can result in a substantial cost for harvesting the algae. Apt K E et al. (1999). Furthermore, all outdoor culture systems are subject to large variations in light intensity and temperature caused by diurnal and seasonal periodicity that makes maintaining maximal productivity and reproducibility problematic.

Numerous designs have also been constructed for the indoor, closed culture of algae using electric lights for illumination. Ratchford and Fallowfield (1992) "Performance of a flat plate, air lift reactor for the growth of high biomass algal cultures," *J Appl. Phycol.* 4: 1-9; Wohlgeschaffen, G D et al. (1992) "Vat incubator with immersion core illumination—a new, inexpensive set up for mass phytoplankton culture," *J Appl. Phycol.* 4:25-9; Iqbal, M et al. (1993) "A flat sided photobioreactor for culturing microalgae," *Aquacult. Eng.* 12:183-90; Lee and Palsson (1994) "High-density algal photobioreactors; using light-emitting diodes," *Biotechnol. Bioeng.* 44:1161-7. These systems are expensive to build and operate and are subject to the same surface-to-volume constraints and problems associated with low density yields as outdoor ponds. Apt K E et al. (1999).

The production costs of phototrophically grown diatoms and other microalgae are very expensive, resulting from low densities and high harvesting costs. Nevertheless for a small number of specific algal products this technology has proven very successful, producing many thousands of tons per year. Lee, Y-K (1997) "Commercial production of microalgae in the Asia-Pacific Tim," *J. Appl. Phycol.* 9:403-11; Apt K E et al. (1999). Major products from photosynthetic microalgae include dried biomass or cell extracts from *Chlorella, Dunaliella* and *Spirulina*. These are primarily produced in large open ponds.

Growing algae heterotrophically in conventional fermentors is a potential alternative to ponds or photobioreactors and a potential means to reduce substantially the cost of growing algae. Day et al. (1991) "Development of an industrial scale process for the heterotrophic production of a micro-algal mollusk feed," *Bioresource Technol.* 38:245-9; Orus et al. (1991) "Suitability of *Chlorella vulgaris* UAM 101 for heterotrophic biomass production," *Bioresour. Technol.* 38:179-184; Barclay et al. (1994) "Heterotrophic production of long-chain omega-3 fatty acids utilizing algae and algae-like microorganisms," *J. Appl. Phycol.* 6:123-9; Gladue and Maxey (1994) "Microalgal feeds for aquaculture," *J. Appl. Phycol.* 6:131-141; Chen F., "High cell density culture of microalgae in heterotrophic growth," *Trends Biotechnol.* 14:421-6 (1996); Apt, K E et al. (1999). The basic principle of fermentor growth is to provide highly controlled optimal growth conditions to maximize productivity.

Typical fermentor culture conditions may be summarized as follows. The culture vessels range in volume from 1 to 500,000 liters and are operated under sterile conditions. A motorized shaft with a series of impellers provides mixing. Sterile air is pumped into the system at high pressure and flow rates to ensure proper gas exchange, and dissolved $O_2$ and $CO_2$ levels are continuously monitored and adjusted. Heating and/or cooling coils regulate temperature and the automatic addition of acid and/or base maintains pH. The culture medium for algal fermentative growth is similar to that used for phototrophic growth, except that glucose or a similar carbohydrate provides both fixed carbon and an energy source in fermentative growth. Other nutrient levels (i.e., nitrogen and phosphorus) are also continuously monitored and adjusted. Culture density may be further increased by using techniques such as chemostat culture, fed-batch culture, or membrane bioreactor culture. More detailed information regarding the growth of microalgae in fermentors can be found in the papers cited herein, which are herein incorporated by reference, and in Apt, K E et al. (1999). See, also, U.S. Pat. No. 5,244,921 to Kyle et al.; U.S. Pat. No. 5,374,657 to Kyle; U.S. Pat. No. 5,550,156 to Kyle; U.S. Pat. No. 5,567,732 to Kyle; U.S. Pat. No. 5,492,938 to Kyle et al.; U.S. Pat. No. 5,407,957 to Kyle, et al.; U.S. Pat. No. 5,397,591 to Kyle et al.; U.S. Pat. No. 5,130,242 to Barclay; U.S. Pat. No. 5,658,767 to Kyle; and U.S. Pat. No. 5,711,983 to Kyle which are also incorporated by reference.

As a result of the high level of process control possible with heterotrophic growth in fermentors, culture conditions and biomass yields are consistent and reproducible, with heterotrophic algal cell densities reported of 50 grams dry biomass per liter to as high as 100 g dry biomass per liter. Gladue and Maxey (1994); Running et al. (1994) "Heterotrophic production of ascorbic acid by microalgae," *J. Appl. Phycol* 6:99-104. These biomass levels are at least 10-fold higher than those achieved by photosynthesis-based culture systems. Radmer R J and Parker B C (1994) "Commercial application of algae: opportunities and constraints," *J. Appl. Phycol* 6:93-98. The high biomass levels also greatly decrease the volume of water that must be processed during harvesting per gram of biomass yield. Because cultures can routinely run in fermentors with volumes greater than 100,000 L, several thousand kilograms of dried biomass can be produced per run. The effectiveness of large-scale cultures and the production of high biomass levels can make the cost of fermentative growth an order of magnitude less expensive than photobioreactors. (Radmer and Parker 1994; Apt K E et al (1999).

The ability to provide complete control over the culture is also critical for maintaining food industry standard Good Manufacturing Practices (GMP), as designated by the Food and Drug Administration. Maintenance of GMP is required for the production of high-quality food- or pharmaceutical-grade materials. Apt K E et al. (1999).

The ability to grow microalgae heterotrophically using microbiological fermentation techniques can dramatically lower the costs associated with their production and provide the high degree of quality control needed for a food grade product. The estimated cost of producing heterotrophic algal biomass can be less than $5 per kilogram. Gladue and Maxey (1994). In contrast, the theoretical cost of producing, algae phototrophically in bioreactors is estimated to be an order of magnitude higher and actual production costs for phototrophic algae at aquaculture facilities are often two orders of magnitude higher. Wilkinson, L. (1998) "Criteria for the design and evaluation of photobioreactors; for the production of microalgae," World Aquaculture Society Annual Meeting, February, Los Vegas, Nev., p. 584; Benemann, J. R. (1992) "Microalgae aquaculture feeds," *J. Appl. Phycol.* 4:232-45. Only a small number of algae are currently produced using fermentation technology; these include *Chlorella*, *Nitzschia alba*, *Tetraselmis*, and *Crypthecodinium*. These algae are able to utilize external organic compounds as energy and carbon sources.

Given the valuable products produced by algae (including algal biomass itself and the difficulties of culturing algae in photosynthetically-based systems, it is highly desirable to culture microalgae in heterotrophic conditions in fermentors. However, a significant restriction on the use of fermentation technology for the production of algal products is that most algae are obligate phototrophs and are therefore unable to be grown using this technology. There therefore exists a need to develop methods for culturing a greater variety of algae under heterotrophic conditions in fermentors.

SUMMARY OF THE INVENTION

The present invention involves the discovery that phototrophic algae may be transformed into heterotrophic algae, which are capable of growth in the dark with only an external source of carbon.

It is an object of the present invention to provide methods for transforming phototrophic algae into heterotrophic algae.

It is another object of this invention to provide such transformed algae.

It is a further object of this invention to provide stable populations of cells transformed according to the methods of the present invention, and to provide methods for producing biomass and other products of phototrophic cells by culturing transformed cells in the dark.

These and other objectives are met by one or more of the following embodiments of this invention.

This invention provides cells that are transformed with genes that encode proteins that enhance or enable heterotrophic growth. In one mode of this embodiment, heterotrophic conversion is accomplished by transforming the cells with only one gene. In another mode, heterotrophic conversion is accomplished by transforming the cells with multiple genes. Cells may be transformed with a gene or genes that encode proteins which affect uptake and catabolism of sugars and/or other exogenous sources of fixed carbon. Alternatively, cells may be transformed with a gene or genes that encode transporters capable of taking up an exogenous fixed carbon source (i.e., a catabolyzable compound). Or cells may be transformed with a gene or genes encoding mono- or disaccharide transporters, especially hexose transporters.

In one embodiment, the present invention provides algal cells, preferably micro algal cells, which grow in the substantial absence of light, even though the cells are from algal strains that are obligate phototrophs, because the cells comprise chimeric DNA encoding a protein which will transport a catabolizable carbon source into the algal cell. Alternatively, the present invention provides algal cells comprising chimeric DNA which encodes a protein that will transport a catabolizable carbon source into the algal cell, where the protein is expressed in an amount sufficient to transport into the cell adequate catabolizable carbon source to support heterotrophic growth of the cell. Preferably, the catabolizable carbon source according to these modes of the invention is a monosaccharide or an oligosaccharide; more preferably, the protein is a disaccharide transporter or a hexose transporter.

In another embodiment, this invention provides a method of producing algal biomass, preferably microalgal biomass, from obligately phototrophic algal strains by culturing algae in the substantial absence of light, preferably in a fermentor, using transformed cells of the algal strain which contain chimeric nucleic acid encoding a protein that, upon expression by the algae, transports a catabolizable carbon source into the algal cells. Preferably, the catabolizable carbon source transported into the algal cells is a monosaccharide or an oligosaccharide; more preferably, the protein encoded by the chimeric nucleic acid is a disaccharide transporter or a hexose transporter. For this embodiment, the protein may be expected to be expressed in an amount sufficient to transport into the cell adequate catabolizable carbon to support heterotrophic growth of the cell.

In yet another embodiment, this invention provides a method for the heterotrophic conversion of cells of an obligately phototrophic organism selected from the group consisting of marine organisms, prokaryotic algae, and eukaryotic algae. The method comprises the steps of (1) transforming the cells with DNA comprising a gene coding for a transporter of a catabolizable carbon source across the cell membrane and (2) selecting for cells capable of growth on the catabolizable carbon source in the dark. In one mode of this embodiment, the obligately phototrophic organism is a marine alga. In a preferred mode, the gene coding for a transporter of a catabolizable carbon source is coupled with a selectable gene, and after transformation, transformed cells are grown on media selective for the selectable gene before selecting for cells capable of growth on the catabolizable carbon source in the dark. In a particularly preferred mode, the selectable gene confers resistance to an antibiotic on the transformed cells, and the selective media contains the antibiotic.

In still another embodiment, this invention provides a method for selecting transformed cells from a cell population exposed to transforming vectors containing a gene of interest. The method comprises transfecting cells of a cell population which is unable to grow in the dark on a source of catabolizable carbon, where the transformation vector comprises a gene of interest in conjunction with a gene whose expression enables growth of the cells on the source of catabolizable carbon in the dark. After the transfection, selection for cells capable of growth in the dark is carried out, and then the selected cells are further tested to determine whether they also contain the gene of interest.

In other embodiments of this invention, cells are transformed with a gene or genes that encode proteins that upregulate an existing transporter of a reduced carbon source (i.e., a catabolyzable compound) across the cell membrane. In other embodiments of this invention, cells are transformed with a gene or genes that encode proteins that activate an existing transporter of a reduced carbon source across the cell membrane. In still other embodiments of this invention, cells are transformed with a gene or genes that encode proteins that facilitate the use of reduced carbon source(s) by the cell.

In another embodiment according to the present invention, autotrophic cells are transformed with a gene of interest in conjunction with a gene or genes encoding protein(s) that enable or enhance heterotrophic growth, and transformation to establish or enhance heterotrophic growth is used as a marker for transformation with the gene of interest. In yet another embodiment of the present invention, heterotrophic cells are mutagenized to render them incapable of growth on a given carbon source, then transformed with a gene of interest in conjunction with a gene or genes which re-establishment of the ability to grow on that carbon source is used as a mechanism for selection, and the re-establishment of growth on the carbon source is used as a marker for transformation with the gene of interest.

A significant restriction on the use of fermentation technology for the production for the production of algal products is that most algae are obligate phototrophs and are therefore unable to be grown using this technology, It has been discovered that obligate phototrophic organisms cannot utilize a fixed carbon source because they do not have the machinery to import the fixed carbon and/or they cannot convert it to a metabolically useful form. The present invention allows circumvention of this restriction by converting phototrophs to cells that are capable of growth on external organic compounds. In order to grow in the dark on an organic substance as a carbon and energy source, a cell must effectively take up the required substance(s) from the surrounding medium and then assimilate it into all components essential for growth via light-independent metabolic reactions.

BRIEF DESCRIPTION OF THE FIGURES

FIG. 2. Southern blot analyses of untransformed *P. tricornutum*: lanes show results for Wild Type and two cell lines transformed with genes encoding glucose transporters. Total DNA was digested with restriction endonuclease. A) Hybridization of DNA from cell line Hup 2 with a DNA probe for the hup coding region. B) Hybridization of DNA from cell line Glut 13 with a DNA probe for the glut coding region.

FIG. 3. Northern blot analyses of untransformed *P. tricornutum*: lanes show results for Wild Type and two cell lines transformed with genes encoding glucose transporters. A) Hybridization of total RNA from cell line Glut 13 with a DNA probe for the glut coding region. B) Hybridization of total RNA from cell line Hup 2 with a DNA probe for the hup coding region.

DETAILED DESCRIPTION OF PARTICULAR EMBODIMENTS

Figure 1:
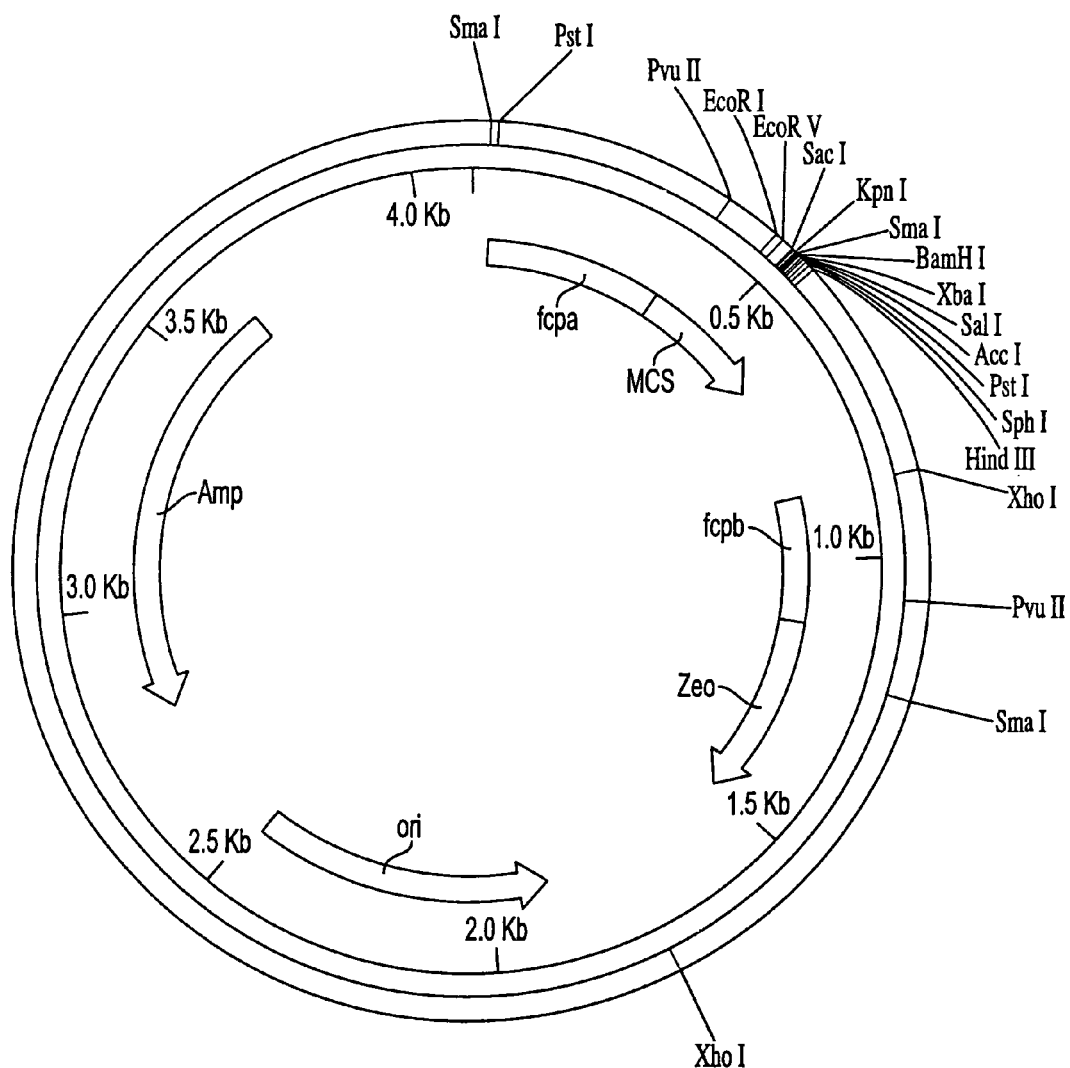
FIG. 1. Map of the *Phaeodactylum* transformation vector pPha-T1 with indicated restriction sites. The sequence of this vector has the Genbank Accession No. AF219942. The fcpA promoter has been placed in front of the multiple cloning site (MCS). The fcpB promoter was placed in front of the sh ble gene. The construct also contains the ampicillin resistance gene (Amp) and the *E. coli* origin of replication. The fcpA terminator region which follows both the MCS and the sh ble regions, is not shown.

There are a number of valuable commercial uses for microalgae. However, commercial-scale production of photosynthetic algae most frequently involves the use of large, outdoor ponds, which present numerous disadvantages. Contaminants frequently invade pond cultures since they remain unshielded from the environment, and seasonal variations and fluctuations in temperature and light conditions make it difficult to predict the rate of growth and final culture densities. Furthermore, self-shading among the algae can severely limit biomass yields. These factors have restricted successful large-scale cultivation of algae to a small subset of organisms that includes *Spirulina* and *Dunaliella* (Apt, et al. (1999) *J. Phycol.*, 35:215).

A strategy that has the potential to dramatically reduce the cost of producing microalgal biomass for commercial uses is to engineer the organisms to grow without light in conventional microbial fermentors. Considerations discussed above suggest that it would be advantageous to engineer micro algal metabolism for high rates of heterotrophic growth. Most photosynthetic organisms (plants, algae, cyanobacteria) are capable of gluconeogenesis for the storage of carbon as sugars. When the carbon supply is limited, these reserves are metabolized for energy using familiar glycolytic mechanisms. The present inventors explored whether photosynthesis could be obviated if a cell could directly import fixed carbon for glycolysis, as with any natural heterotroph.

Most diatoms do not have the capacity to grow in the absence of light on exogenous glucose (Droop, 1974). A 'metabolic block' that prevents heterotrophic growth of diatoms was postulated to result from the inability of the cells to take up or further metabolize sugars. The present inventors have demonstrate herein that trophic conversion of the obligate photo autotrophic diatom, *P. tricornutum*, can be achieved by transforming the alga with a single gene encoding a glucose transporter. Strains transformed with either the Hup1 gene of *C. kessleri* or the Glut1 gene of humans are able to take up glucose and grow in the dark with glucose as the sole source of reduced carbon. These results clearly demonstrate an engineered trophic conversion of an obligate photoautotrophic organism into a heterotrophic organism. While Hup1 has also been expressed in the green alga *Volvox* (Hallman, et al., 1996) and the diatom Cylindrotheca (Fischer, et al., 1999), neither of these transformed strains were able to grow heterotrophically.

Conversion of a phototrophic alga to one capable of growth on, e.g., glucose as the only carbon source requires the introduction of genes encoding the required functions. In order for an obligate phototroph to be converted to a heterotroph, the phototroph must acquire competence for growth when supplied with an exogenous source of fixed carbon. Thus, conversion of a phototrophic alga to one capable of growth in the dark on an external organic substance, such as glucose, as the sole carbon and energy source requires the introduction of a gene or genes encoding the required functions (e.g., transporters, hexokinase, etc.).

Previous attempts to convert obligate phototrophic algae into heterotrophic algae have failed. Although algae transformed to express sugar transporters have been shown to be capable of taking up glucose, none of these algae have been able to grow in the dark.

The present invention provides a method for converting obligate phototrophic cells into heterotrophic cells, which are capable of growth in the dark. There is no obvious precedent for this type of conversion, so it has been difficult to predict what types of complications will be encountered. According to the present invention, at the simplest level, only a hexose transporter is required for the conversion. The discovery by the present inventors that heterotrophic conversion can be accomplished by the insertion of a single gene (e.g., a gene encoding a transporter capable of taking up an exogenous fixed carbon source, such as a gene encoding a hexose transporter) is surprising considering the complexity of heterotrophic metabolism and the previous failures in the art.

Of course, because heterotrophic growth is a complex process, heterotrophic growth may be enhanced by introduction of multiple genes that code for proteins that enhance or enable the uptake and/or catabolism of sugars and/or other exogenous sources of fixed carbon. In the present invention, phototrophic algae is transformed with one or more genes affecting uptake and catabolism of sugars and/or exogenous source of fixed carbon. The cells are transformed with these genes using a suitable transformation vector. Preferably, the gene(s) inserted under the control of a promoter will result in expression of the gene(s) in the transformed cells.

DEFINITIONS

In describing the present invention, the following terminology is used in accordance with the definitions set out below.

"Heterotrophic conversion" is the conversion of a phototrophic, autotrophic, or auxotrophic organism that is incapable of growth on, or which grows poorly on, a given organic carbon and energy source (e.g., glucose), to an organism capable of heterotrophic growth, or improved heterotrophic growth, on that same carbon source. For cells to be heterotrophically converted, it is necessary that they be capable of growth in the dark. It is not required that the cells remain in constant or complete darkness.

"Catabolism" is metabolic breakdown or degradation of a complex molecule (i.e. glucose, or other carbon source) into simpler products, primarily for the production of energy. A "catabolizable carbon source" is a complex molecule, typically a mono- or oligo-saccharine, an amino acid, or other biochemical molecule, that can undergo catabolism in a biological cell.

"Improved growth" is intended to encompass any improvement. As non-limiting examples, improvement could comprise more rapid growth, more rapid production of a desired product, or growth which may be sustained for longer periods of time. Likewise, poor growth" is intended to encompass any growth-related feature which is sought to be improved. Both "poor growth" and "improved growth" are relative terms and quantitative levels denoting poor or improved for one characteristic or organism may not be poor or improved for another characteristic or organism.

A "protein which can enable or enhance heterotrophic growth" is meant to be interpreted broadly to encompass any protein that (1) makes it possible or assists in making it possible for a cell which was incapable of growth on a given carbon source to grow on that carbon source, (2) makes it possible or assists in making it possible for a cell which grew poorly on a given carbon source to exhibit improved growth on that carbon source, or (3) makes it possible or assists in making it possible-for a cell which was initially capable of growth on a given carbon source to exhibit improved growth on that carbon source. Such proteins include, but are not limited to, transporters of carbon compounds across the cell membrane, proteins which catabolize carbon compounds, and proteins which upregulate and/or activate such transporters or catabolizing proteins.

A "phototroph" is an organism capable of converting light energy to chemical energy.

An "autotroph" is an organism cells that uses inorganic material as a source of nutrients and $CO_2$ as its source of carbon.

An "obligate phototroph" is an organism that requires light energy for the production of chemical energy and is incapable of using exogenously supplied performed organic molecules as its sole source of carbon or energy.

A "heterotroph" is an organism that can use preformed organic compounds as the source of carbon and energy in the absence of light. Heterotrophs can, therefore, grow independently of illumination; for example, heterotrophs can grow in the dark, in the light, and in partial light. Similarly, "heterotrophic growth" refers to growth which does not require light to occur and can, therefore, occur independent of the level or lack of illumination.

"Auxotrophs" are organisms which require a certain substance to grow. For example, a given auxotroph may be unable to produce a specific amino acid and will therefore require that amino acid for growth. Many auxotrophs are phototrophs. According to the present invention, heterotrophic conversion includes the conversion of an organism that is incapable of growth (or which grows poorly) on an external carbon source such as glucose to an organism capable of growth (or which grows well) on that external carbon source.

"Phototroph," "autotroph," and "auxotroph" may all be used interchangeably to indicate an organism that does not grow, or that grows poorly, on the external carbon source, e.g., glucose, on which it is sought to be grown. Because these organism grow poorly or do not grow at all on external carbon sources, they may also be referred to as obligate photo-, auto-, or auxotrophs in the context of this invention.

As used herein, "growth (or culture) in substantial darkness (or substantial absence of light)," "grown (or cultured) in substantial darkness (or substantial absence of light)," and like phrases indicate that the growing or culturing is carried out under light conditions under which phototrophic cells would be unable to grow or would grow very poorly. Similarly, "substantial darkness" and "substantial absence of light" are synonymous and indicate a level of illumination which may vary between total darkness and the level at which phototrophic cells cannot grow or grow very poorly. Expressed in an alternative manner, the level of illumination indicated by the phrases "in the dark," "substantial absence of light," and like phrases is a level of illumination which would be growth-limiting (in terms of, as non-limiting examples, doubling time, maximum culture density, or product production) for phototrophic cells. Hence, growth or culture in the dark encompasses, as non-limiting examples, growth in fermentors having windows or openings for observing the cells, feeding the cells, and the like, so long as light entering the fermentor is insufficient to support long-term growth of obligate phototrophs in culture.

A "chimeric DNA" is an identifiable segment of DNA within a larger DNA molecule that is not found in association with the larger molecule in nature. Thus, when the chimeric DNA encodes a protein segment, the segment coding sequence will be flanked by DNA that does not flank the coding sequence in any naturally occurring genome. Allelic variations or naturally occurring mutational events do not give rise to a chimeric DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide in vivo. A polyadenylation signal and transcription termination sequence will usually be located 3' to the coding sequence.

A "promoter sequence" is a DNA regulatory region capable of binding RNA polymerase in a cell and initiating transcription of a downstream coding sequence. A coding sequence is "under the control" of the promoter sequence when RNA polymerase which binds the promoter sequence will transcribe the coding sequence into mRNA, which is then in turn translated into the protein encoded by the coding sequence. For purposes of defining the present invention, the promoter sequence is bounded at its 3' terminus by the translation start codon of a coding sequence and extends upstream (5' direction) to include at least the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Promoters will usually contain additional consensus sequences (promoter elements) for more efficient initiation and transcription of downstream genes.

A "genetic fusion" according to this invention is a chimeric DNA containing a promoter and a coding sequence that are not associated in nature.

A "replicon" is any genetic element (e.g., plasmid, chromosome, virus) that functions as an autonomous unit of DNA replication in vivo; i.e., capable of replication under its own control.

Vectors are used to introduce a foreign substance, such as DNA, RNA or protein, into an organism. A "DNA vector" is a replicon, such as plasmid, phage or cosmid, to which another DNA segment may be attached so as to bring about the replication of the attached segment.

A cell has been "transformed" by exogenous DNA when such exogenous DNA has been introduced inside the cell wall. Exogenous DNA may or may not be integrated (covalently linked) to chromosomal DNA making up the genome of the cell. For example, the exogenous DNA may be maintained on an extrachromosomal element (or replicon) such as a plasmid. A stably transformed cell is one in which the exogenous DNA has become integrated into a chromosome so that it is inherited by daughter cells through chromosome replication. This stability is demonstrated by the ability of the cell to establish cell lines or clones comprised entirely of a population of daughter cells containing. the exogenous DNA.

"Salt" as used in herein refers to an inorganic ionic compound which is commonly found in sea water or a mixture of such compounds. The concentration of salt is expressed herein as the amount of such compounds that provide the ionic equivalent to a given weight of sodium chloride. The salt concentration of seawater is about 32-33 g/L.

Algae which are obligate phototrophs, (both macro- and micro-algae) may be converted to heterotrophs by the method of this invention. Many algae are obligate phototrophs, which are incapable of growth on glucose, and any of these organisms are potential targets for trophic conversion. Lists of phototrophs may be found in a review by Droop (Droop M R "Heterotrophy of Carbon." In *Algal Physiology and Biochemistry, Botanical Monographs*, 10: 530-559, ed. Stewart W D P, University of California Press, Berkeley (1974)); and a representative, non-exclusive list of phototrophic algal genera with potential or known commercial value is provided below (Table A), grouped at the phylum level. The "common name" is in parenthesis.

TABLE A

Exemplary List of Phototrophic Algae

| | |
|---|---|
| Cyanophyta (Blue-green algae) | - *Spirulina, Anabaena*. |
| Chlorophyta (Green algae) | - *Dunaliella, Chlamydomonas, Heamatococcus*. |
| Rhodophyta (Red algae) | - *Porphyridium, Porphyra, Euchema, Graciliaria*. |
| Phaeophyta (Brown algae) | - *Macrocystis, Laminaria, Undaria, Fucus*. |
| Baccilariophyta (Diatoms) | - *Nitzschia, Navicula, Thalassiosira, Phaeodactylum*. |
| (Some members of these genera are capable of heterotrophic growth on glucose, but not others.) | |
| Dinophyta (Dinoflagellates) | - *Gonyaulax*. |
| Chrysophyta (Golden algae) | - *Irsochrysis, Nannochloropsis* |
| Cryptophyla | - *Crypromonas*. |
| Euglenophyta | - *Euglena*. |

*Phaeodactylum tricornutum* has been one of the most widely utilized model systems for studying diatoms, particularly in areas of ecology, physiology, and biochemistry. See, Ianora A, Poulet S A, Miralto (1995), "A comparative study on the inhibitory effect of diatoms on the reproductive biology of the copepod *Temora stylifera*," *Mar. Biol.* 121:533-539; Kuma K, Matsunga K (1995); "Availability of colloidal ferric oxides to coastal marine phytoplankton," *Marine Biol.* 122:1-11; Alwyn T, Rees V (1995), "On ammonia futile cycling in a marine unicellular alga," *Biochem. Biophys. Acta.* 1228:254-260; La Roche I et al. (1995), "Flavodoxin expression as an indicator of iron limitation in marine diatoms," *J. Phycol.* 31:520-530; Rees TAV et al. (1995), "In situ glutamine synthetase activity in a marine unicellular alga. Development of a sensitive colorimetric assay and the effects of nitrogen status on enzyme activity." *Plant Physiol.* 109: 1405-1410; Khalyfa A et al. (1995) "Purification and characterization of chlorophyllase from the alga *Phaeodacrylum tricornitum* by preparative native electrophoresis," *Appl. Biochem. Biotech* 53:11-27; Zhukova N N, Alzdaischer N A (1995), "Fatty acid composition of 15 species of marine microalgae," *Phytochemistry* 39:351-356. Recently it has also been employed as a molecular model to study some of the unique biological processes found in diatoms, particularly involving plastid protein targeting and cell wall formation. Apt K E, Clendennen S K, Powers D A, Grossman A R (1995) "The gene family encoding the fucoxanthin chlorophyll proteins from the brown alga *Macrocystis pyrifera*," *Mol. Gen. Genent.* 246:455-64; Apt K E et al. (1994), "Characterization of genes encoding the light-harvesting proteins in diatoms: biogenesis of the fucoxanthin chlorophyll a/c protein complex," *J Appl. Phycol.* 6:225-230, Bhaya D, Grossman AG (1993) "Characterization of gene clusters encoding the fucoxanthin chlorophyll protein of the diatom *Phaeodactylum tricornutum*," *Nucleic Acids Research* 21:4458-68).

The microalga *Phaeodactylum tricornutum* has been repeatedly reported to be unable to utilize external glucose, acetate, amino acids, etc, as the sole energy or carbon source. Cooksey K E "Acetate metabolism by whole cells of *Phaeodactylum tricornutum*," *J. Phycol.* 10:253-7 (1974); Droop 1974; Hellebust J A, Lewin J "Heterotrophic Nutrition," in (Werner D ed.) *The Biology of Diatoms, Botanical Monographs* 13:169-197, University of California Press, (1977). The present inventors have repeatedly examined this microalga and observed no detectable growth or nutrient uptake in the dark on media containing glucose. The recent development of a genetic transformation system has provided new opportunities to study the molecular mechanisms for the biological processes in organisms such as *Phaeodactylum*. (WO 97/39106 and U.S. Pat. No. 6,027,900 to Allnutt et. al., both entitled: "Methods and Tools for Transformation of Eukaryotic Algae," both incorporated herein by reference). As a result, *Phaeodactylum tricornutum* was selected as a model to test the ability to convert an obligate phototrophic organisms through the use of genetic engineering.

Transformed cells are produced by introducing exogenous DNA into a population of target cells and selecting the cells which have taken up the exogenous DNA, usually by measuring expression of some determinant present on the exogenous DNA but missing from the non-transformed cells. A preferred selective marker for use in algae is the Zeocin (Invitrogen) resistance selection system described in WO 97/39106. See, also, U.S. Pat. No. 6,027,900 to Allnutt et al. Briefly, resistance to zeocin (and related antibiotics) has been discovered to be maintained in high salt medium to a much greater extent than is observed for other antibiotic resistance genes. Thus, transformants containing exogenous DNA with a zeocin resistance determinant will grow in salt water in the presence of suitable concentrations of zeocin, while non-transformed cells of marine organisms will not.

Standard methods for construction of chimeric DNA and its use in transformation of cells and expression of proteins therein are familiar to the skilled worker, and these methods have been described in a number of texts for standard molecular biological manipulation. (See, e.g., Packer & Glaser, 1988, "Cyanobacteria", *Meth. Enzymol.*, Vol. 167; Weissbach & Weissbach, 1988, *Methods for Plant Molecular Biology*, Academic Press, New York; Sambrook, J., Maniatis, T., & Fritsch, E. F. (1989) *Molecular Cloning: A Laboratory Manual*, 2nd ed., Cold Spring Harbor Press, Cold Spring Harbor, N.Y.; and Clark M S, 1997, *Plant Molecular Biology*, Springer, New York.

The chimeric nucleic acid of the present invention, e.g., a nucleic acid construct comprising a coding sequence which encodes a protein which can enable or enhance heterotrophic growth fused to a suitable promoter, may be introduced into cells of, e.g., marine organisms or eukaryotic algae alone or as part of a DNA vector. Suitable vectors for use in marine organisms or eukaryotic algae are known in the art and any such vector may be used. Even vectors which do not replicate in algae can be useful, if recombination between the vector and the genome occurs.

To summarize the process of constructing a vector, the upstream DNA sequences of a gene expressed under control of a suitable promoter may be restriction mapped and areas important for the expression of the protein characterized. The exact location of the start codon of the gene is determined and, making use of this information and the restriction map, a vector may be designed for expression of a heterologous protein by removing, the region responsible for encoding the gene's protein but leaving the upstream region found to contain the genetic material responsible for control of the gene's expression. A synthetic oligonucleotide multicloning site is preferably inserted in the location where the protein coding sequence once was, such that any gene (e.g., a protein coding sequence) could be cloned in using restriction endonuclease sites in the synthetic oligonucleotide. An unrelated gene (or coding, sequence) inserted at this site would then be under the control of an extant start codon and upstream regulatory region that will drive expression of the foreign (i.e., not normally associated with the regulatory sequences of the vector) protein encoded by this gene. Once the gene for the foreign protein is put into a cloning vector, it can be introduced into the host organism using any of several methods, some of which might be peculiar to the host organism.

DNA delivery methods which are within the skill of the art include silica carbide whisker vortexing, glass bead vortexing, electroporation, and particle bombardment. Preferably, glass bead vortexing is used. More preferably, particle bombardment is used. These methods may be used to introduce the genetic fusion of the present invention into cells of, e.g., marine organisms or eukaryotic algae alone or as part of a DNA vector.

Variations on these methods are amply described in the general literature references cited herein. Manipulation of conditions to optimize transformation for a particular host is within the skill of the art.

Suitable transformation vectors include those having at least one site for inserting a gene coding for a protein that enhances or enables heterotrophic growth. Preferably, transformation vectors used in the methods according to the present invention have at least an insertion site for insertion of a gene coding for a transporter capable of taking up an exogenous fixed carbon source. More preferably, transformation vectors used in the methods according to The present invention—have at least an insertion site for insertion of a gene encoding a hexose transporter. Typically, transformation vectors are also able to replicate in bacteria, so that large amounts of the vector can be prepared easily, using methods such as those described in Sambrook, I., Maniatis, T., & Fritsch, E. F. (1989) *Molecular Cloning: A Laboratory Manual.* 2nd ed., Cold Spring Harbor Press, Cold Spring Harbor, N.Y. Preferably, vectors will be chosen which are known to transfect the host algal species.

Transformation systems have been described for a limited number of eukaryotic algal genera, including diatoms. For example, four species of diatoms have been transformed. In each case a special vector was developed for the diatom of interest. The present inventors transformed *Phaeodactylum*, using the vector called pPha-T1, which will be described in more detail below. *Cyctotella cryptica* and *Navicula saprophila* have been transformed using vectors pAC-CNPT10 and pACCCNPT5.1, which have the nptII gene (neomycin phosphotransferase) conferring resistance to the antibiotic G418. The promoter driving expression of introduced gene was from the endogenous acc gene (acyl-CoA carboxylase). Dunahay, T. G., Jarvis, E. E. & Roessler, P. G. (1995) "Genetic transformation of the diatoms *Cyclotella cryptica* and *Navicula saprophila*," *J Phycol.* 31:1004-12. *Cylindrotheca fusiformis* has been transformed by Fisher et al. (Fischer H., Robl, I., Sumper, M., & Kroger, N., (1999), "Targeting and covalent modification of cell wall and membrane proteins heterologously expressed in the diatom *Cylindrotheca fusiformis* (Bacillariophyceae)," *J. Phycol.* 35:113-20). In this case, the sh ble gene, which confers resistance to the antibiotic zeocin was utilized. The promoter driving expression was from the endogenous fru gene, which encodes for a cell wall protein, and the vector was called pble/fruE A derivative of this vector, pble/HUPtag, containing the hup1 gene encoding the glucose transporter from *Chlorella*, was also used to transform *Cylindrotheca fusiformis*. The transformed alga was able to take up glucose. However, the transformed alga was unable to grow heterotrophically (Fischer, et al., 1999).

A small number of green algae have been transformed (see Stevens and Purton (1997) "Genetic engineering of eukaryotic algae: progress and prospects," *J. Phycol.* 33:713-22). The most prominent is *Chlamydomonas*. This algae has been a significant molecular model system for many years with numerous labs involved in research. As a result there are a large number of described vectors that could be used for trophic conversion of this alga. *Volvox*, a genus that is closely related to *Chlamydomonas*, has also been transformed (Hallman A, Sumper M (1996) "*The Chlorella hexose*/H' symporter is a useful selectable marker and biochemical reagent when expressed in *Volvox*," *Proc. Natl. Acad. Sci.* 93:669-673). Hallmann and Sumper introduced the *Chlorella hup* gene into *Volvox*. The alga was sensitive to deoxyglucose, indicating the transporter was functioning. However, the authors did not provide uptake measurements and the cells did not grow heterotrophically.

Preferred vectors for this invention are vectors developed for one or more algal systems. Furthermore, the methods described herein and the Zeocin resistance selection system provide one skilled in the art with guidance for the preparation and selection of vectors appropriate for transformation of phototrophic algae into heterotrophic algae.

Different promoters may be more or less effective in different host systems. For example, the promoter from a gene associated with photosynthesis in one photosynthetic species may be used to direct expression of a protein in transformed algal cells or cells of another photosynthetic marine organism. Suitable promoters for use in the present invention may be isolated from or synthesized based on known sequences from other photosynthetic organisms. Preferred promoters include those for genes from other photosynthetic species, including other algae and cyanobacteria, which are homologous to the photosynthetic genes of the algal host to be transformed. Preferably, the promoters chosen for use according to the present invention provide for constitutive, high level production of the chimeric genes they control in the organisms in which they are used. Preferably, this constitutive, high level production is independent of illumination, so that it occurs both in light and in the absence of light. Examples of such promoters are the promoters for constitutively expressed genes such as housekeeping genes. Given the reporter gene systems now available, selection of a promoter with the desired characteristics is well within the ability of one in the arts of molecular biology, psychology, and the like. See, Zaslayskaia, et al.

For a particular algal host, it may be preferable to identify the homologous light harvesting gene from that host and isolate the homologous promoter from the host organism to get optimal expression. However, it has been found for Some organisms that foreign promoters give excellent or less restricted expression in the host relative to the homologous promoter of the host organism (Mermet-Bovier, et al. (1993) *Curr. Microbiol.* 26:323-327).

In one embodiment, the gene(s) desired to be expressed is regulated by a promoter of a chlorophyll binding protein. A series of light harvesting promoters from the fucoxanthin chlorophyll binding proteins have now been identified and cloned from *Phaeodactylum tricornutum* by the present inventors. See, Apt, et al. (1996). The use of fcp promoters for transformation of algae, especially photosynthetic diatoms, is described in WO 97/39106. See, also, U.S. Pat. No. 6,027,900 to Allnutt et al. Suitable promoters include the fcpA, fcpB, fcpC, and fcpE promoters, as well as many other lhc (light harvesting complex) promoters. Other suitable promoters which are apparent to the skilled worker may be used for heterotrophic conversion according to this invention.

A general-purpose transformation vector, pPha-T1 (FIG. 1) has been constructed to facilitate efficient introduction of heterologous genes into the diatom *P. tricornutum*. This vector contains a multiple cloning site with ten unique restriction sites for inserting genes of interest. The promoter and terminator regions of the fcpA gene flank the multiple cloning site to promote efficient expression of the inserted genes. The primary selection for *P. tricornutum* cells harboring the vector is zeocin resistance, which is encoded by the sh ble gene flanked by the *P. tricornutum* fcpB promoter and the fcpA terminator.

The plasmid transformation vector pPha-T1 (FIG. 1) was constructed in several stages. The first step involved subcloning the fcpA terminator region from pfcpA/ble (Apt, et al., 1996) into the HinDIII-XhoI sites of pSP73 (Promega). The zeocin resistance cassette from pfcpB/ble (Apt et al., 1996), which contains the fcpB promoter driving the sh ble gene, was subcloned as a XhoI fragment into the pSP73 XhoI site. The fcpA promoter region from pfcpA/ble (Apt et al., 1996) was subcloned as a PstI-EcoRI fragment and inserted into Bluescript SK–. This same fragment was then removed as a BamHI-EcoRV fragment and ligated into the BglII-EcoPV sites of pSP73 to form the final basic construct. The multicloning site from pSP73 between the EcoRV and HinDIII sites was preserved intact, excluding the ClaI site, which was removed by site-directed mutagenesis to eliminate a cryptic ATG start codon (Deng, W. P. & Nickotoff, J. A., (1992) "Site-directed mutagenesis of virtually any plasmid by eliminating a unique site," *Anal. Biochem.* '1100:81-8; Zaslayskaia, et al., 2000).

Plasmid transformation vector pPha-T1 may be used to transform diatoms such as *Cyclotella, Cylindrotheca*, and *Nitzschia alba* by particle bombardment. The skilled worker may also use alternative transformation vectors, based on homologous promoters, which can be prepared by methods used to prepare the pPha-T1 vector. WO 97/39106. See, also, U.S. Pat. No. 6,027,900 to Allnutt et al.

The ability of a given promoter to regulate gene expression, as well as the timing of such expression and factors affecting such expression, in any particular species of algae can be evaluated using the Zeocin selection system described in WO 97/39106. See, also, U.S. Pat. No. 6,027,900 to Allnutt et al. Additional selection systems which can be used to evaluate promoters and their activity in a given organism are described in Zaslayskaia, et al., 2000).

In order to easily detect the transfer of genetic material to any organism, i.e., in order to detect whether a cell has been transformed, phenotypic trials indicating this transfer need to be established. The trait most conveniently, and therefore traditionally, manipulated has been antibiotic sensitivity. The lowest concentrations of zeocin and nourseothricin which completely abrogate growth in various organisms may be determined using the methods elaborated for *P. tricornutum* in WO 97/39106. See, also, U.S. Pat. No. 6,027,900 to Allnutt et al., and Example 1, below. Additional selection systems which can be used to detect the transfer of genetic material to an organism are described in Zaslayskaia, et al. (2000).

Suitable coding sequences for use in the genetic constructs of the present invention include genes for proteins that enhance or enable heterotrophic growth. Preferably, coding sequences are genes that encode proteins which affect uptake and catabolism of sugars and/or other exogenous sources of fixed carbon. More preferably, coding sequences are genes that encode transporters capable of taking up an exogenous fixed carbon source. Non-limiting examples of such carbon sources include sugars, fatty acids, amino acids, pyruvate, glycerol, and citrate. Even more preferably, coding sequences are genes encoding mono- or disaccharide transporters, such as, but not limited to, sucrose transporters. Most preferably, coding sequences are genes encoding hexose transporters, such as, but not limited to, glucose transporters.

Other non-exclusive examples of coding sequences which are suitable for in the genetic constructs of the present invention include coding sequences that encode proteins that upregulate existing transporters of reduced carbon sources across the cell membrane, coding sequences that encode proteins that activate existing transporters of reduced carbon sources across the cell membrane, and coding sequences that encode proteins that facilitate the catabolism of reduced carbon sources by the cell.

The inventors have discovered that expression of a single exogenous gene encoding a transporter for a compound that serves as a catabolyzable carbon source may be sufficient to convert an obligate phototroph to a recombinant cell capable of heterotrophic growth. In preferred embodiments of this invention, transfection with a single gene effects the phototroph-to-heterotroph conversion. Of course, introduction of a plurality of genes may be necessary or desirable to achieve more ample heterotrophic growth, and constructs using combinations of suitable coding sequences may be used according to this invention. For example, sequences encoding transporters for different compounds or transporters in conjunction with enzymes involved with metabolism of the compounds may be used.

Hexose transporters comprise a superfamily of related sugar transporters that all consist of a structure having 12 membrane-spanning domains. See, e.g., Walmsley A R et al. (1998) "Sugar transporters from bacteria, parasites and mammals: structure-activity relationships," *Trends. Biochem. Sci.* 23(12):476-81 (a broad general review); Henderson P J, (1990) "The homologous glucose transport proteins of prokaryotes and eukaryotes," *Res. Microbiol.* 141(3):316-28; Bisson L F et al., (1993) "Yeast sugar transporters," *Crit. Rev. Biochem. Mol. Biol.* 28(4):259-308; Kruckeberg (1996); Mueckler M et al., (1997); Barrett M P et al., (1998) "Trypanosome glucose transporters," *Mol. Biochem. Parasitol.* 91(1):195-205; Caspari T et al. (1994) "Hexose/H+ symporters in lower and higher plants," *J. Exp. Biol.* 196; 483-491. An exemplary list of characterized hexose transporters is given in Table B, along with examples of characterized sucrose, citrate, and fatty acid transporters. See, Hirsch D. et al., (1998) "A family of fatty acid transporters conserved from mycobacterium to man," *Proc. Natl. Acad. Sci. U.S.A.* 95(15): 8625-8629; Heisterkamp N. et al., (1995) "Localization of the human mitochondrial citirate transporter protein gene to chromosome 22Q11 in the DiGeorge syndrome critical region," *Genomics* 29(2): 451-456; Rentsch D et al., (1998) "Structure and function of plasma membrane amino acid, oligopeptide and sucrose transporters from higher plants," *J. Membr. Biol.* 162(3):177-90. Table B also includes an exemplary list of amino acid transporters. See, Saier M H, (2000) "Families of transmembrane transporters selective for amino acids and their derivatives." *Microbiology* 146:1775-95; Meredith D, and Boyd C A. (2000) Structure and function of eukaryotic peptide transporters. *Cell Mol Life Sci* 57(5):754-78; Ortiz-Lopez A, Chang H, and Bush D R. (2000) "Amino acid transporters in plants." *Biochim Biophys Acta* 1465(1-2):275-80; and McGivan J D. (1996) "Mammalian amino acid transporters and their regulation: introduction." *Biochem Soc Trans.* 24(3):837-8.

TABLE B

Examples of characterized transporters of reduced carbon sources
(i.e., catabolyzable compounds)

Examples of characterized hexose transporters

Yeast - hxt 1-7, gh rl
Mammals - glutI, glut4
Trypanosomes - tht
Plants - stpl-4
Algae - hupl, hup2
Cyanobacteria - glcP
Bacteria - xylE, galP

Examples of characterized sucrose (disaccharide) transporters

Plant - sutl, sut2, sucl

Examples of characterized citrate transporters

Mammalian - ctp
Bacteria - cit

Examples of characterized fatty acid transporters

Mammalian - fatp
Yeast - , pxalp, fatlp

Examples of amino acid transporters

Plant - aap1-5
Mammalian - ngt1
yeast - ort1
bacteria - gap1

Since the different sugar transporters are related, any of them may be used as a transporter in trophic conversion according to the present invention. The present inventors have successfully converted phototrophic algae to heterotrophs by inserting glut1 (mammalian hexose symporter) or hupl (algal hexose symporter). The present inventors have discovered that insertion of glut1 is particularly successful in converting phototrophic algae into heterotrophs. Experiments with hxt1, hxt2, hxt4 (yeast hexose symporters) were less successful. The lesser success experienced when transforming *Phaeodactylum* with yeast transporter genes is most likely the result of mismatched codon usage. For example, the yeast transporters use a codon bias which does not match the *Phaeodactylum* codon usage.

Many algae have been shown to have unusual codon usages (Bhaya D., Grossman A G (1993) "Characterization of gene clusters encoding the fucoxanthin chlorophyll protein of the diatom *Phaeoductylum tricornutum*," *Nucleic Acids Research* 21:4458-159; Apt K E, Hoffman N, Grossman A R (1993) "The Y subunit of R-phycoerythrin and its possible mode of transport into the plastid of red algae," *J Biol. Chem.* 268:16208-15; Apt K E, Clendennen S K, Powers D A, Grossman A R (1995) "The gene family encoding the fucoxanthin chlorophyll proteins from the brown alga *Macrocystis pyrifera*," *Mol. Gen. Genent.* 246:455-64). The codon usage in *P. tricornutum* is very similar to that of humans in that the arginine codons AGA and AGG are rarely used (Bhaya et al., 1993); Apt, et al., 1995). Previous attempts to express in *P. tricornutum* heterologous genes which contained a preponderance of the AGA codon all failed. The present inventors have determined that the infrequent use of codons AGA and, especially, AGG, are important for appropriate gene expression. To date, there have not been any genes cloned from, or successfully expressed in *P. tricornutum* that contain a predominance of the codon AGG. According to the present invention, all *P. tricornutum* transformations are therefore preferably done with genes that do not contain these codons (or at least rarely contain them).

Briefly, the DNA sequence of a protein of interest is determined. Undesirable codons are identified. Using point mutagenesis, these undesirable codons are replaced by desirable codons coding for the same amino acid. The newly reconstructed genes are then inserted into vectors and used to transform species of interest. In this way, heterogeneous proteins can be tailored to be efficiently expressed in organisms of interest. Therefore, any genes related to uptake and use of sugar and/or other exogenous sources of fixed carbon may be reconstructed by such techniques and used to convert phototrophs to heterotrophs using the methods of the present invention. For example, the yeast hexose transporters (the protein products of the hxt genes) may be used more successfully to convert *Phaeodactylum* by reconstructing the hxt genes to reduce or eliminate the use of codons AGA and AGG.

Alternatively, codon usage can be changed by reconstructing the gene' using conservative amino acid substitution (Zolotukhin S, Potter M, Hauswirth W M, Guy J, Muzyczka N (1996) "A 'humanized' green fluorescent protein cDNA adapted for high-level expression in mammalian cells," *J. Virology,* 70:4646-4654; Haas J, Park E C, Seed B (Mar. 1, 1996) "Codon usage limitation in the expression of HIV-1 envelope glycoprotein," *Curr. Biol.* 6(3):315-24). "Conservative amino acid substitutions" are the substitution of one amino acid residue in a sequence by another residue of similar properties, such that the secondary and tertiary structure of the resultant peptides are substantially the same. Conservative amino acid substitutions occur when an amino acid has substantially the same charge as the amino acid for which it is substituted and the substitution has no significant effect on the local conformation of the protein. Amino acid pairs which may be conservatively substituted for one another are well-known to those of ordinary skill in the art.

Whether a given gene has been successfully expressed in a given transformed cell (as determined by using the Zeomycin resistance selection system) can be determined using the methods of the present invention. Successful expression of a gene or genes useful for converting phototrophic cells to heterotrophic cells may be measured by the ability of the transformed cells to take up an external source of fixed carbon (e.g., glucose, acetate) or to grow in the dark. Preferably, successful expression of a gene or genes useful for converting phototrophic cells to heterotrophic cells is measured by both the ability of the transformed cells to take up an external source of fixed carbon and to grow in the dark. Control cells for use in determining the success of expression in this context can be negative controls (e.g., cells of the transformant species which have not been transformed or other phototrophs) and/or positive controls (e.g., naturally occurring heterotrophs or phototrophic cells which have previously been converted to heterotrophs).

A DNA sequence encoding a gene encoding a protein useful for the uptake and/or use of an exogenous source of carbon may be inserted in the chosen vector by ordinary recombinant DNA techniques to create a vector which will produce expression of the protein of interest. For example, a DNA sequence encoding a hexose transporter protein may be used to create a hexose transporter (HX) vector. A population of the vector, e.g. the HX vector, may be obtained by expansion of the vector in bacterial culture, for vectors capable of replication in bacteria, or by PCR or other amplification techniques. The expanded population of vectors, e.g. HX vectors, is then used to transform a population of the chosen host cells.

Transformation may be carried out by any suitable technique, including electroporation, DNA-coated microparticle bombardment, silica carbide whisker vortexing, and glass bead vortexing. Preferably, glass bead vortexing or microparticle bombardment is used. More preferably, particle bombardment is used. Such techniques are well-known in the art and are described in greater detail herein and in WO 97/39106. See, also, U.S. Pat. No. 6,027,900 to Allnutt et al.

When microparticle bombardment using the Bio-Rad Biolistic PDS-1000/HE™ particle delivery system is employed (according to the manufacturer's instructions), preferably 1100, 1350, or 1500 psi rupture discs are used, although any psi rupture disc may be used. Most preferably, 1500 psi rupture discs are used. Similarly, any microparticles commonly used in the art may be used for bombardment. Preferably, tungsten particles M5 (0.4 µm median diameter) or M17 (1.1 µm median diameter) or gold particles of 1 micron median diameter are used. Most preferably, tungsten particles M17 are used. The cells to be bombarded may be placed on any level within the chamber. Preferably, the cells are placed on level two or three. Most preferably, the cells are placed on level two. Preferably, the DNA coated onto the microparticles is supercoiled.

In a preferred mode of the invention, successful transformants are selected in a first selection step, based on a characteristic of the vector such as resistance to an antibiotic, and only the successful transformants are tested in a second step for the ability to grow autotrophically using the substrate of interest (i.e., external source(s) of fixed carbon on which the transforming gene(s) should enable the transformed cells to grow). In another preferred mode, after the transformation step, cells are grown in reduced light in the presence of low concentrations of the reduced carbon source whose utilization is enabled by the transformation, e.g., sugar, and the transformed host cells are subcultured into media with successively increasing substrate concentrations to allow the transformed host to adapt to heterotrophic growth. Where the substrate of interest is glucose, the selection step may be testing the cells for ability to take up $^{14}$C-glucose or for sensitivity to the toxic glucose analog, 2-deoxyglucose. Preferably, light is withdrawn and the transformed cells are tested for their ability to grow in the dark on the substrate of interest.

For example, DNA encoding a glucose transporter protein may be inserted into a vector containing an antibiotic resistance gene, such as resistance to phleomycin. The resultant HX vector is used to transform algal cells, and after the transformation step, the cells are plated out on media containing the antibiotic phleomycin and grown in the light. Colonies which appear represent cells that have acquired antibiotic resistance as a result of successful transformation with the HX vector. These transformed cells are then plated out on media containing low sugar concentration (e.g., 0.1% glucose). Colonies which grow in low light or in the dark on the low-sugar medium are replated onto media containing a higher glucose concentration (e.g., 1% glucose). The cells which are able to grow in the dark on these high sugar plates are heterotrophic recombinant algae.

The trophic conversion method of this invention produces recombinant algae capable of heterotrophic growth. These recombinant algae may be grown in fermentors to high cell numbers without the problem of starvation due to self-shading which occurs in phototrophic algae. Thus, algal cell products may be obtained in higher yield from fermentor culture of the recombinant algae of this invention which compared with the yield from culture of the parent phototrophic algae. Further genetic modification of the recombinant algae may be pursued by traditional mutation methods or recombinant methods or both. Culturing the modified cells in the dark or in substantial darkness on substrate-containing (e.g., sugar) medium will maintain the heterotrophic nature of the cells, because the absence of light or substantial absence of light provides selective pressure suppressing cells losing the DNA encoding the hexose transporter or other converting gene(s).

This invention also contemplates methods of using the recombinant heterotrophic algae for culturing in fermentors to produce desired algal products. Thus, this invention provides a method for obtaining algal biomass or algal cell products comprising culturing in a fermentor recombinant algal cells expressing, e.g., a heterologous hexose transporter protein and harvesting the biomass and/or the desired algal cell product(s). Media and culture conditions for both plating out the recombinant algae and for fermentor culture may be readily determined by the ordinary artisan through routine optimization. See, also, U.S. Pat. No. 5,244,921 to Kyle et al.; U.S. Pat. No. 5,374,657 to Kyle; U.S. Pat. No. 5,550,156 to Kyle; U.S. Pat. No. 5,567,732 to Kyle; U.S. Pat. No. 5,492,938 to Kyle et al.; U.S. Pat. No. 5,407,957 to Kyle, et al.; U.S. Pat. No. 5,397,591 to Kyle et al.; U.S. Pat. No. 5,130,242 to Barclay, U.S. Pat. No. 5,658,767 to Kyle; and U.S. Pat. No. 5,711,933 to Kyle.

Products which may be produced by algae include, but are not limited to, pigments (e.g., β-carotene, phycobiliproteins, carotenoids, xanthophylls), oils with nutritional value (e.g., docosahexaenoic acid), and isotopically-labeled biochemicals (e.g., $^{13}$C- or $^{14}$C-glucose).

This invention also contemplates the use of algal biomass, either before or after extraction or partial extraction of desired products, as an animal feed. A non-limiting example is the use of the biomass as an aquaculture feed for, e.g., larvae, ratifers, artemia, shrimp, fish, mollusks, vertebrates, or invertebrates. Other non-limiting examples are the use of the biomass to feed, e.g., fowl, cattle, or pigs. The biomass may also be used as a food or nutritional composition for humans.

The present inventors have also discovered that the methods of the present invention may be used as or to create a selection system for detecting and/or selecting for transformed algae. These methods are particularly useful in transformation of an organism which is able (either in its wild type state or through the heterotrophic conversion of the present invention) to grow on a given carbon source in the dark. Mutagenesis is used to disrupt a gene or genes necessary to and/or helpful in uptake and/or catabolism of that carbon source. Means for mutagenizing cells are well known in the art. Non-limiting, non-exclusive examples of methods for mutagenizing cells include chemical mutagenesis, radiation-induced mutagenesis, gene replacement, and site-directed mutagenesis.

Where gene replacement is used to inactivate the gene sought to be inactivated, a gene construct is produced containing the gene sought to be inactivated with an antibiotic selectable marker inserted into the middle of the coding region, resulting in a non-functional coding region of the gene sought to be inactivated. The gene construct is then inserted into the cells by methods described herein. Where the non-functional copy of the gene sought to be inactivated integrates and replaces the endogenous; functional gene, the cells is rendered, e.g., unable or less able to grow on the carbon source the catabolism of which the disrupted gene facilitated.

Cells which are unable or less able to grow on the carbon source may be detected by various methods, such as assaying for the cells' ability to take up that carbon source or to grow on that carbon source in the dark. Where the gene which has been inactivated is a gene involved in glucose uptake, the cells can easily be tested for inactivation of the gene of interest by growing them on the toxic glucose analog deoxyglucose. Cells possessing a functional glucose transporter will import this compound. The deoxyglucose will enter the cells and not be metabolized. As a result it will accumulate within the cells to toxic levels, killing the cells. Cells that can grow in the presence of deoxyglucose will likely not be able to take up this compound, and, thus, they have been transformed as desired. That the cells can not take up deoxyglucose or glucose can be confirmed by glucose uptake assays and the inability of the cells to grow in the dark on glucose as the sole carbon source.

Where a gene has been inactivated by gene replacement and an antibiotic selectable marker has been inserted, cells with disrupted genes can easily be selected for by growing the cells on the antibiotic, thereby selecting the resistant cells. Confirmation that the cells cannot take up and/or catabolize a given carbon source can be tested by uptake assays and/or assays for determining the cells' ability to grow on that carbon source in the dark.

A strain which has been rendered unable or less able to grow on a given carbon source may then be transformed with other genes of interest in conjunction with transformation with a gene which will restore the cells' ability to grow in the dark on a particular carbon source. In this way, the ability to grow on a particular carbon source can be used as a selectable marker for transformation, in a manner similar to that in which antibiotic resistance is used as such a marker. Cells which have been successfully transformed may be selected by growing the cells in the dark on the particular carbon source.

In a similar manner, the introduction of a gene or genes encoding protein(s) that enable or enhance the growth of cells on a particular carbon source on which they we re previously unable or less able to grow (as is described herein) may also be used as a selectable marker. In such a system, cells would be transformed with a gene of interest in conjunction with their transformation with a gene or genes encoding protein(s) that enable or enhance the growth of cells on a particular carbon source on which they were previously unable or less able to grow.

In this way, the ability to grow on a particular carbon source can be used as a selectable marker for transformation, in a manner similar to that in which antibiotic resistance is used as such a marker. Cells which have been successfully transformed may be selected by growing the cells in the dark—on the particular carbon source.

Introduction or reintroduction of a gene encoding a protein enabling or enhancing uptake or growth on a particular carbon source would be accomplished by methods described herein. The vector design would be similar to that described herein, except that a gene encoding a protein enabling or enhancing uptake or growth on a particular carbon source would replace the antibiotic selectable marker. Guidance in carrying out transformations and selection are provided herein.

As the cells of the present invention are able to grow heterotrophically and may be used as a transformation selection system, this invention contemplates the use of these cells to produce recombinant protein. In such an application, autotrophic cells or cells the ability' of which to grow in the dark on an external carbon source, has been disrupted through mutagenesis are transformed with a gene encoding the recombinant protein sought to be made and a gene or genes encoding protein(s) that enable or enhance heterotrophic growth. If desired, an antibiotic selection system, as described herein, may. be used to assist in the initial screening of the cells for transformation. The cells which have undergone heterotrophic transformation are then selected using the methods described herein. The selected cells are tested for their ability to produce the recombinant protein of interest. These cells which produce the protein can then be grown in fermentors under heterotrophic conditions, and the protein isolated therefrom using techniques which are well-known to those skilled in the art.

The trophic conversion of microalgae such as diatoms is a critical first step in the engineering of algae for successful large-scale cultivation using microbial fermentation technology. In addition to providing a means for rigorously maintaining specific culture conditions with the objective of maximizing productivity, the use of fermentation technology will eliminate contamination of the cultures by microbes, which is an important criterion for maintaining food industry standards as dictated by the U.S. Food and Drug Administration. Furthermore, sugars such as glucose, as well as other growth-limiting nutrients, can be continuously provided to the cultures such that growth rates remain saturated. Efficient fermentation has permitted the cultivation of the microalga *Crypthecodinium* for production of the polyunsaturated fatty acid DHA for use in human nutrition (Kyle, D. J., (1996) *Lipid Technology,* 2:106). Optimizing conditions for fermentative growth of naturally heterotrophic algae has resulted in dry biomass accumulation to 100 gm/liter (Gladue, et al., 1999; Running, et al., 1994) which is 10-50 fold higher than the yields obtained using light-dependent culture systems. Increased biomass accumulation in fermentor systems results in production costs that are at least an order of magnitude less than those incurred using pond culture production methods (Radmer, et al., 1994). This reduced cost increases the feasibility for developing a large range of algal products, including polyunsaturated fatty acids (e.g. EPA), carotenoids and xanthophyHs (e.g. (-carotene, lutein, filcoxanthin, astaxanthin), feeds for aquaculture and a variety of pharmaceuticals and nutraceuticals for market production. But the results also have important implications with respect to fundamental biological aspects of marine ecosystems. Approximately 50% of the carbon fixation occurs in oceans, and the oceans serve as a major sink for fixed carbon (Raven, et al. (1999) *Plant Cell and Environm.,* 22:741). The diatoms contribute substantially to the reduction of inorganic carbon in marine habitats, and their contribution may increase substantially as the ecology of oceanic environments are altered (M. R. Landry, et al., (2000) *Marine Ecology Progress Series,* 201:57); B. Boyle, (1998) *Nature* 393:733; Takeda, (1998) *Nature* 393:777). The exploitation of diatoms that can be genetically manipulated and that can grow heterotrophically will facilitate the use of mutants to augment our utilization of both photosynthesis and other metabolic pathways in algae that are essential for maintaining marine ecosystems.

EXAMPLES

In order to facilitate a more complete understanding of the invention, a number of Examples are provided below. However, the scope of the invention is not limited to specific embodiments disclosed in these Examples, which are for purposes of illustration only.

Example 1

Antibiotic Sensitivity in Diatoms

The diatoms *Phaeodactylum tricornutum, Cylindrotheca fusiformis, Cyclotella cryptica* and *Nitzschia alba* were extensively tested for sensitivity to a series of antibiotics for which resistance genes are available, and the lowest concentrations which completely abrogate growth were determined for each antibiotic (Table C). Most of the antibiotics had no significant effect on growth or were effective only at very high concentrations compared to their effectiveness in abrogating growth of other eukaryotic organisms. These include antibiotics such as G418, Hygromycin, Kanamycin and Spectinomycin, which are routinely utilized for selection of other eukaryotic organisms.

For the diatoms tested, only the antibiotics zeocin and phleomycin resulted in cell death in 100% I.O. media (see Example 4 for description of media and growth conditions).

It was found that by lowering the concentration of the media to 50% I.O. or less the sensitivity of the diatoms to antibiotics greatly increased. The effective concentration range of the antibiotic in most cases was lowered by a factor of 10. Representative diatoms were further tested against three of the more effective antibiotics at lower concentrations of media.

Cells of each diatom species were plated on solid media at salinity equivalents of 25-100% I.O. media, with a gradient of antibiotic concentrations. After 2 weeks of illumination the growth of the cells was assessed and the concentration of antibiotic required for cell death was determined. (Table D).

TABLE C

Effect of antibiotics on the growth of selected diatoms. Values represent the lowest concentration of the antibiotic per ml required for cell death or the highest concentration tested.

| Antibiotics | P. tricornutum | C. fusiformis | C. cryptica | N. alba |
|---|---|---|---|---|
| Neomycin | >1 mg | >1 mg | >1 mg | >1 mg |
| Kanamycin | >1 mg | >1 mg | >1 mg | >1 mg |
| Gentamicin | >1 mg | >1 mg | >1 mg | >1 mg |
| Streptomycin | >1 mg | >1 mg | >1 mg | >1 mg |
| Spectinomycin | >1 mg | >1 mg | >1 mg | >1 mg |
| G418 | >1 mg | >1 mg | 250 mg | >500 mg |
| Hygromycin | >1 mg | 500 mg | >500 mg | >500 mg |
| Nourseothricin | 250 mg | >250 mg | >250 mg | >250 mg |
| Puromycin | 200 mg | 100 mg | 100 mg | 100 mg |
| Chloramphenicol | 200 mg | 100 mg | 50 mg | 50 mg |
| Erythromycin | 100 mg | 100mg | 50 mg | 50 mg |
| Bleomycin | >50 mg | >50 mg | N.D. | N.D. |
| Phleomycin | 5 mg | 25 mg | 25 mg | >50 mg |
| Zeocin | 50 mg | >250 mg | 250 mg | >250 mg |

TABLE D

Effect of antibiotics on the growth of selected diatoms in media with reduced salinity. The relative percentage of salinity verses normal seawater of the medium is given in parentheses. Antibiotic levels are given as the lowest concentration of antibiotic per ml required for cell death or the lowest concentration tested.

| | P. tricornutum | C. fusiformis | C. cryptica |
|---|---|---|---|
| Zeocin | 25 mg (50%) | 250 mg (50%) | <5 mg (10%) |
| | | 100 mg (25%) | |
| Nourseothricin | 25 mg (50%) | 50 mg (50%) | <5 mg (10%) |
| | 10 mg (25%) | <10 mg (25%) | |
| Phleomycin | <5 mg (50%) | 25 mg (50%) | <5 mg (10%) |
| | <5 mg (25%) | <5 mg (25%) | |

Example 2

P. tricornutum is Incapable of Heterotrophic Growth

To confirm that P. tricornutum was incapable of heterotrophic growth on glucose, cells were repeatedly plated on glucose containing solid media and placed in the dark. Cells typically divided up to 1-2 times over 24 hrs, then stopped growth. No additional divisions were evident after 1-2 months. Cultures were also checked for glucose transporter activity. No detectable uptake was evident even after 4 hours of incubation. Cells were also plated on 16 different hexose or related sugars (arabiose, cellobiose, fructose, fucose, galactose, gluconate, lactose, maltose, maltobiose, mannose, meliblose, nibose, sorbitol, suclose, trehalose, xylose), with no detectable growth.

Example 3

Generic Mutation does not Enable Heterotrophic Growth of P. tricornutum

To confirm that P. tricornutum is not capable of spontaneous mutations that result in the ability to grow in the dark on glucose, $10^{10}$ control cells were plated onto glucose-containing solid media. No spontaneous colonies formed on glucose. To confirm that the transformation procedure and/or insertion of foreign DNA could not result in trophic conversion, approximately 100 cell lines were transformed with pPha-T1 containing a variety of heterologous genes (uidA gfp, nat, and nptII), but not glut1 or hup1, and these transformed cell lines were tested for growth on glucose in the dark. None grew on glucose.

Example 4

Transformation of P. tricornutum for Heterotrophic Growth

Phaeodactylum tricornutum is one microalga that can be genetically modified by transformation (Zaslayskaia, et al. (2000), Apt, et al. (1996)), but that is unable to grow heterotrophically (Cooksey, 1974; Droop, 1974; Hellebust, et al., 1977). A trophic conversion of this alga was attempted by transforming it with genes encoding glucose transporters. The glucose transporter genes used for transformation included Glut1, from human erythrocytes (Mueckler, et al., 1997), Hup1 from *Chlorella kessleri* (Sauer, et al., 1989), and Hxt1, Hxt2, Hxt4 from *Saccharomyces cervisiae* (Kruckeberg, 1996). The coding regions of these genes were inserted into the P. tricornutum transformation vector pPha-T1, which uses the promoter of a gene encoding the fucoxanthin chlorophyll binding proteins (Fcp) to drive expression of foreign genes in diatoms (Barclay, et al., 1994; Zaslayskaia, et al., 2000). A construct was also generated in which the GFP gene was fused to the 3' end of the Glut gene. Plasmids were introduced into P. tricornutum using biolistic procedures and transformants were selected for Zeocin resistance in the light (Zaslayskaia, et al., 2000). The transformants were then transferred to solid or liquid medium containing 0.1 or 1.0% glucose, placed in complete darkness and monitored for growth.

Culture Conditions *Phaeodactylum tricornutum* Bohlin (University of Texas Culture Collection, strain 646) was grown at 20° C. with continuous illumination at 75 mmol photons $M^{-2}s^{-1}$ in Provasoli's enriched seawater medium made with Instant Ocean™ (I.O) artificial seawater, instead of natural sea water, at 0.5× concentration. See, Stair, R. C. & Zeikus, J. A. (1993) "UTEX—The culture collection of algae at the University of Texas at Austin," *J. Phycol.* 29 (Suppl):93. Solid medium contained 1.2% agar and liquid cultures were bubbled with air containing 1% $CO_2$ in Roux bottles.

Constructs: The sequence of the *Phaeodanylum* transformation vector pPha-TI (see FIG. 1) has the Genbank accession No. AF219942. The fcpA promoter has been placed in front of the multiple cloning site (MCS). The fcpB promoter was placed in front of the sh ble gene. The construct also contains the ampicillin resistance gene (Amp) and the *E. coli* origin of replication.

pPha-T1 (FIG. 1) was constructed in several stages. The first step involved subcloning the fcpA terminator region from pfcpA/ble (Apt et al. 1996) into the HindIII-XhoI sites of pSP73 (Promega). The zeocin resistance cassette from pfcpB/ble (Apt et al. 1996), which contains the fcpB promoter driving the sh ble gene, was subcloned as a XhoI fragment into the pSP73 XhoI site. The fcpA promoter region from pfcpA/ble (Apt et al. 1996) was subcloned as a PstI-EcoRI fragment and inserted into Bluescript SK−. This same fragment was then removed as a BamHI-EcoRV fragment and ligated into the BgIII-EcoRV sites of pSP73 to form the final basic construct. The multi-cloning site from pSP73 between the EcoRV and HindIII sites was preserved intact, excluding the ClaI site, which was removed by site-directed mutagenesis (Deng and Nickoloff 1992) to eliminate a cryptic ATG start codon. The pPha-T1 vector contains ten commonly used, unique restriction sites into which genes of interest can be inserted.

A series of glucose transporters were tested for expression in *P. tricornutum*. These include the hxt1, hxt2, htx4 genes from *Saccromyces cerviesae*, the *Chlorella kessleri* hup1 gene, and glut1 found in erythrocytes. Kruckeberg A L (1996) "The hexose transporter family of *Saccharomyces cerevisiae*," *Arch. Microbiol.* 166:283-92; Sauer N, Tanner W (1989) "The hexose carrier from *Chlorella* cDNA cloning of a eucaryotic H+-cotranporter," *FEBS Lett* 259:43-46; Mueckler M, Hresko R C, Sato M (1997) "Structure, function and biosynthesis of GLUTI," *Biochemical Society Transactions* 25:951-4. The coding regions of these genes were inserted into the transformation vector pPha-T1.

Plasmids used for construction of transformation vectors used to introduce glucose transporters into cells of *Phaeodactylum* were constructed by adding appropriate restriction sites by PCR and inserting the coding region for the transporter of interest into pPha-T1. Plasmid pGlut-Phat used primers GLUTPHAT5' (GACTGGATCCATGGAGCCCAGCAG-CAAG) (SEQ ID NO:1) and GLUTPATT3' (GAC-TAAGCTTTCACACTTGGGAATCAGC) (SEQ ID NO:2). Plasmid pHup-Phat used primers HUPPHAT5' (GATGAAT-TCATGGCCGGCGGTGGTGTAG) (SEQ ID NO:3) and HUPPHAT3' (GACTAAGCTTTTACTTCATCGC-CTTTGAC) (SEQ ID NO:4). Plasmid pHxt2-Phat used primers HXT2PHAT5' (GGGAATTCATTCAAGATGTCT-GAGTTCGCTAGAAG) (SEQ ID NO:5) and HXT2PHAT3' (CCCCGCATGCTTATTCCTCGGAAACTCTT) (SEQ ID NO:6). Plasmid pHxt-Phat used primers HXT4PHAT5' (GGGAATCATTCAGGATGTCTGAAGAAGCT) (SEQ ID NO:7) and HXT4PHAT3' (CCTCTAGATTACTTTTTTC-CGAACATC) (SEQ ID NO:8).

Microparticle Bombardment: Cells were bombarded with the transformation vector containing the gene of interest using the Bio-Rad Biolistic PDS-1000/He Particle Delivery System fitted with 1,500 psi rupture discs. Tungsten particles M17 (1.1 μm median diameter) were coated with 0.8 mg plasmid DNA in the presence of CaCl2 and spermidine, as described by the manufacturer. Approximately $5 \times 10^7$ cells were spread in the center one third of a plate of solid 0.5×I.O. medium 1 h prior to bombardment. The plate was positioned at the second level within the Biolistic chamber for bombardment. Bombarded cells were illuminated for 24 h (cells divided once during this period) prior to suspension in 0.5 ml of sterile 0.5×I.O. medium; 100 μL of this suspension (~1× $10^7$ cells) was plated onto solid medium containing 100 μg/ml Zeocin. The plates were placed under constant illumination (75 μmol photons $m^{-2}s^{-1}$) for 2-3 weeks and resistant colonies were re-streaked on fresh solid medium containing at least 100 μg/ml Zeocin.

Colonies of primary transformants were restreaked on 250 μg/ml Zeocin. After two weeks cells were restreaked on media containing 0.1% and 1.0% glucose, and were kept in darkness by wrapping with several layers of foil. After 4 weeks transformants that had detectable growth were restreaked and maintained on 1.0% glucose. Liquid cultures were grown in IO media with 1.0% glucose at 20° C. on an orbital shaker.

Each zeocin resistant cell line was also checked for glucose uptake. All of these transformants resulted from independent particle bombardments.

Glucose Uptake and Growth on Glucose: 250-500 ml of transformed *Phaeodacrylum* cells in logarithmic phase growth were harvested at 2000 rpm for 10 min, washed 2 times with 50% I.O., resuspended in I.O. and counted. Cells were aliquoted into 50 ml tubes (7 ml/tube). Unlabelled glucose was added from a stock solution of 0.1M in 50% I.O. to the appropriate concentration. $D-^{14}C$-glucose (ICN) was added to a concentration of 0.05 μCi per mL. Samples (1 ml) were taken at 1 min intervals, cells were filtered on nitrocellulose and washed 3 times with 50% I.O. containing 5% unlabeled glucose. The filters were transferred to scintillation vials with 10 ml of Scintisafe (Fisher), incubated for 1 hr and counted. Heat-killed or aldehyde fixed cells were used as controls.

For glut1 containing transformants, 22 out of 32 zeocin resistant cell lines were capable of detectable glucose uptake. Uptake rates ranged from a high of 8.8 to 2.0 nmole·$(10^8$ cells·min.$)^{-1}$ (Table E). Cells lines with uptake rates of 1.6 nmole glucose $(10^8$ cell·min$)^{-1}$ or greater (11 of 28) were able to grow on glucose in the dark. For hup1 containing transformants 14 out of 25 antibiotic resistant cell lines were capable of glucose uptake. The uptake rates ranged from 1.72 to 0.06 nmole·$(10^8$ cells·min.$)^{-1}$ (Table F). Cell lines with uptake rates of 0.29 nmole·$(10^8$ cells·min.$)^{-1}$ or greater (11 of 25) were able to grow in the dark. None of the *P. tricornutum* transformants transformed with vectors containing the yeast transporters were capable of detectable glucose uptake. The presence of the hxt 1, 2, or 4 genes or the gene products within cells was not confirmed. The inability of the transformants to express functional Hxt protein may reflect striking differences in codon usage between yeast and *P. tricornutum* (Zaslayskaia, et al., 2000).

Eleven of the glut1 and 11 of the hup1 containing transformants had detectable growth on agar plates or in liquid media containing 0.1% glucose after 2-4 weeks in complete darkness. Glut1 containing transformants with uptake rates greater than 2.0 nmole·$(10^8$ cells·min.$)^{-1}$ were all capable of growth in the dark on glucose. All Hup1 containing transformants with glucose uptake rates greater than 0.29 nmole·$(10^8$ cells·min.$)^{-1}$ cells were capable of heterotrophic growth.

To confirm that the transformation procedure and/or insertion of foreign DNA did not result in trophic conversion, approximately 100 cell lines transformed with pPha-T1 containing a variety of heterologous genes (uidA gfp, nat, and nptII), but no glucose transporters, were plated on glucose (0.1%) containing solid media. None of these cell lines had detectable grow after 4 weeks in the dark.

Heterotrophic growth rates were determined for transformants Glut-13, Glt-17, and Hup-2. All three cell lines had division rates of approximately 0.7 divisions per day.

TABLE E

Glucose uptake rates of glut1 containing transformants of *P. tricornutum*. Uptake rates are expressed as nmole · ($10^8$ cells · min.)$^{-1}$. Cells lines capable of heterotrophic growth are designated with a "+" cells that had no growth are designated as "–".

| Strain | Uptake Rate | Growth |
|---|---|---|
| Glut-28 | 8.8 | + |
| Glut-13 | 7.6 | + |
| Glut-26 | 5.9 | + |
| Glut-25 | 4.9 | + |
| Glut-17 | 4.6 | + |
| Glut-34 | 3.9 | + |
| Glut-11 | 3.5 | + |
| Glut-21 | 3.2 | + |
| Glut-15 | 2.6 | + |
| Glut-1 | 2.4 | + |
| Glut-32 | 1.9 | – |
| Glut-24 | 1.8 | – |
| Glut-3 | 1.6 | + |
| Glut-9 | 1.6 | + |
| Glut-12 | 1.4 | – |
| Glut-3 | 0.94 | – |
| Glut-7 | 0.93 | – |
| Glut-19 | 0.90 | – |
| Glut-22 | 0.82 | – |
| Glut-2 | 0.48 | – |
| Glut-20 | 0.25 | – |
| Glut-10 | 0.20 | – |
| Glut-4 | 0.0 | – |
| Glut-5 | 0.0 | – |
| Glut-6 | 0.0 | – |
| Glut-14 | 0.0 | – |
| Glut-18 | 0.0 | – |
| Glut-23 | 0.0 | – |
| Glut-29 | 0.0 | – |
| Glut-30 | 0.0 | – |
| Glut-31 | 0.0 | – |
| Glut-33 | 0.0 | – |

TABLE F

Glucose uptake rates of hup1 containing transformants of *P. tricornutum*. Uptake rates are expressed as of nmole · ($10^8$ cells · min.)$^{-1}$. Cells lines capable of heterotrophic growth are designated with a cells that had no growth are designated as "–".

| Strain | Uptake Rate | Growth |
|---|---|---|
| Hup-2 | 1.72 | + |
| Hup-12 | 1.40 | + |
| Hup-15 | 1.40 | + |
| Hup-23 | 1.40 | + |
| Hup-24 | 0.94 | + |
| Hup-4 | 0.84 | + |
| Hup-8 | 0.70 | + |
| Hup-10 | 0.68 | + |
| Hup-18 | 0.53 | + |
| Hup-13 | 0.43 | + |
| Hup-9 | 0.29 | + |
| Hup-6 | 0.26 | – |
| Hup-20 | 0.24 | – |
| Hup-25 | 0.06 | – |
| Hup-1 | 0 | – |
| Hup-3 | 0 | – |
| Hup-5 | 0 | – |
| Hup-7 | 0 | – |
| Hup-11 | 0 | – |
| Hup-14 | 0 | – |
| Hup-16 | 0 | – |
| Hup-17 | 0 | – |
| Hup-19 | 0 | – |
| Hup-21 | 0 | – |
| Hup-22 | 0 | – |

Example 5

Incorporation of Desired Genetic Inserts

Cells lines Glut-17 and Hup-2 were used to examine the integration and expression of the respective glucose transporters. Based on Southern blots (see, FIG. 2), Glut-17 appears to have one copy of glut1 and Hup-2 probably has multiple copies of hup1. RNA blots (see, FIG. 3) indicate that each cell line produces a transcript of the expected size.

Preparation of Nucleic Acids: For the preparation of total DNA, the cells were pelleted by centrifugation (5,000×g for 10 min), lysed in 50 mM Tris-HCl, pH 8.0, 10 mM EDTA, 1.0% SDS, 10 mM DTT, 10 µg/ml protease K, 20 µg/ml RNAse A and incubated at 37° C. for 15 min. The lysate was extracted with one volume of phenol:chloroform (1:1) and again with one volume of chloroform. The aqueous phase was collected and made 1.2 g/ml CsCl and 0.2 mg/ml ethidium bromide prior to centrifugation in a Beckman V665.2 rotor for 6 h at 55,000 rpm. The DNA band was collected, extracted with butanol, precipitated with 2 volumes of ethanol and resuspended in TE (10 mM Tris-HCl, pH 8.0, 1 mM EDTA) to a final concentration of 1 mg/ml. RNA was extracted using the method of Chomczynski, (1994, "Single-step method of total RNA isolation by acid guanidine-phenol extraction." In: Celis J. E. (ed) Cell Biology: a laboratory handbook, Vol I. Academic Press, San Diego, pp 680-683).

Gel Electrophoresis and Hybridization Conditions: DNA was resolved on agarose gels in TAE buffer (Maniatis et al. 1982). Nucleic acids were transferred to Nytran filters (Schleicher and Schuell) and cross-linked with UV light using a Stratalinker (Stratagene). Hybridizations were performed in a Bachofer rotary oven at 65° C. overnight in 5×SSFE, 1% SDS, 5×Denhardt's and 100 µg/ml DNA, according to standard protocols (Sambrook et al. 1989). Following hybridizations, the filters were washed three times for 30 min at the hybridization temperature in 50 mM phosphate buffer containing 0.1% SDS. The filters were then dried and exposed to X-ray film for 1 to 4 d (Kodak XAR5). Total RNA was resolved on an agarose gel containing formaldehyde according to the method of Rosen, et al. (1990, "Optimizing the Northern blot procedure," *Biotechniques* 8:398-403).

Example 6

Localization of the Protein Expressed from the Inserted Gene

A more detailed characterization was performed for a number of the Glut transformants, including Glut-17 and Glut GFP-40. The latter strain was transformed with pPha-T 1 harboring the glut1 gene fused to GFP. Transformed cells were broken using a MinibeadBeater by two breakage cycles at full speed (30 sec for each cycle with 3-5 mm cooling on ice between cycles), and the membranes were pelleted by centrifugation at 100,000×g for 30 and then solubilized in 2% SDS. The solubilized proteins were resolved on a 7.5% polyacrylamide gel, transferred to nitrocellulose membranes (Towbin, et al. (1979) *Proc. Natl. Acad. Sci. USA*, 76:4350) and the Glut1 or GFP proteins were detected immunologically (Liscum, et al., (1995) Plant Cell, 7:473). Mono specific antibodies against the Glut1 polypeptide and GFP were used to demonstrate accumulation of Glut1 or the Glut1GFP fusion protein in transformed cell lines.

Figure 4A:
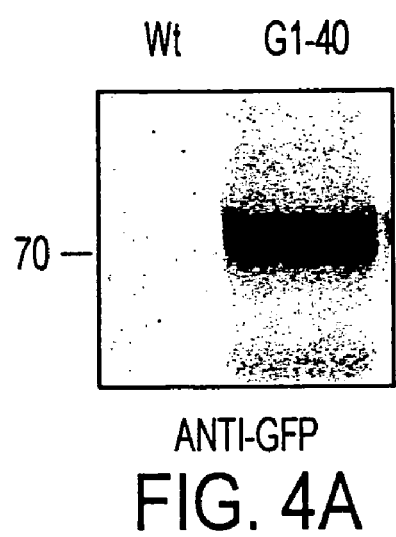
FIG. 4. Reactivity of antibodies specific for Glut1 or GFP to membrane proteins extracted from untransformed and transformed cell lines. The proteins were resolved by SDS-PAGE following solubilization of total membranes from Wt, untransformed cells; G1-40, the Glut1GFP-40 transformant; B, human erythrocytes; Glut1-17, the Glut 1-17 transformant. The antibodies used were specific for GFP (left panel) or Glut1 (right panel).
Figure 4B:
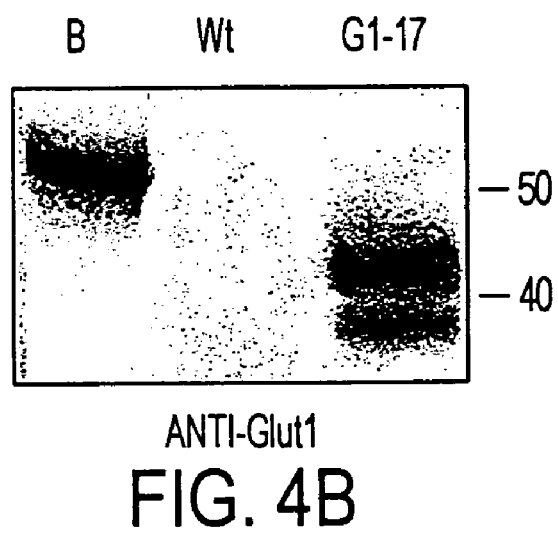

Membranes of the Glut-17 transformant contained two prominent polypeptides that reacted with Glut1-specific antibodies (FIG. 4). These polypeptides had molecular masses of 44 and 39 kDa, which is less than that of the native protein (approximately 55 kDa) synthesized in human erythrocytes (FIG. 4, compare lanes B and G1-17), but which is close to the size of unglycosylated Glut1 (38 kDa) (Asano, et al. (1991) J. Biol. Chem., 266:24632). This implies that the Glut1 that accumulates in *P. tricornutum* is glycosylated differently than in human erythrocytes. The Glut1GFP fusion protein present in the Glut1 GFP-40 transformant had a molecular mass of approximately 75 kDa, which is also slightly smaller than the expected size of Glut1GFP (82 kDa).

To determine the subcellular location of the Glut 1 protein in transformed lines, the Glut1GFP-40 strain was examined for GFP fluorescence by confocal microscopy. Cells were gently smeared onto coverslips (#1½) and mounted in a thin layer of artificial seawater. Confocal microscopy was performed using a Nikon 60×N.a.=1.2 water immersion objective on a Nikon TMD 200 inverted microscope outfitted with a BioRad MRC 1024 confocal head mounted in a Koehler configuration. EGFP was excited at 488 nm and visualized with a 522/25 nm bandpass filter. Plastid autofluorescence was excited at 456 nm and visualized with a 585 nm long pass filter. Images were adjusted in Adobe Photoshop such that control and experimental images were treated identically. Only linear adjustments of contrast and brightness were performed on the original images.

While nontransformed cells showed strong chlorophyll fluorescence in the red fluorescence channel, only a small amount of fluorescence was observed in the green channel (FIG. 6, top panel). Cells transformed to express GFP from the vector pPha-T1 exhibited intense GFP fluorescence in a pattern consistent with localization in the cytosol and the lumen of the cell nucleus (FIG. 6, lower left). A similar distribution of soluble GFP in plant cells has been observed (Chiu, et al. (1996) *Curr. Biol.*, 6:325; Haseloff, et al. 1997) *Proc. Natl. Acad. Sci. USA*, 94:2122). In contrast, when the Glut1GFP chimeric construct is introduced into diatom cells the majority of the fluorescence is associated with the extreme periphery of the cells (FIG. 6, lower right). These results demonstrate that the Glut 1 protein targets GFP to the cell cortex, a pattern consistent with localization of the chimeric protein to the cytoplasmic membrane and the function of Gluti as a cytoplasmic membrane-associated transporter.

Example 7

Kinetics of Glucose Uptake by Transformed Cells

Detailed glucose uptake kinetics were done on various glut containing transformants, which grew well on glucose containing media. 250-500 ml of transformed *P. tricornutum* cells in logarithmic phase growth were harvested at 4,500 rpm (SA600 rotor) for 10 mm, washed 2 times, resuspended in and counted all with 50% 1.0. medium. Assays were initiated by adding unlabelled glucose (to the appropriate concentration) from a stock solution of 0.1M in 50% I.O. and D-$^{14}$C-glucose (ICN) to 0.05 µCi per mL; the cells were maintained in the light during the assay. Samples (800 µl) were withdrawn from the assay mixture at specific time intervals (0, 2, 5, 10 and 15 mm) following the addition of the labeled glucose. The cells were filtered onto Supor (polyethersulfone) membranes (Gelman Scientific) and washed with 50% I.O. medium containing 1% unlabeled glucose. The membranes were transferred to scintillation vials with 5 ml of Scintisafe (Fisher), incubated for 1 h, at 20° C. and then counted.

Figure 5:
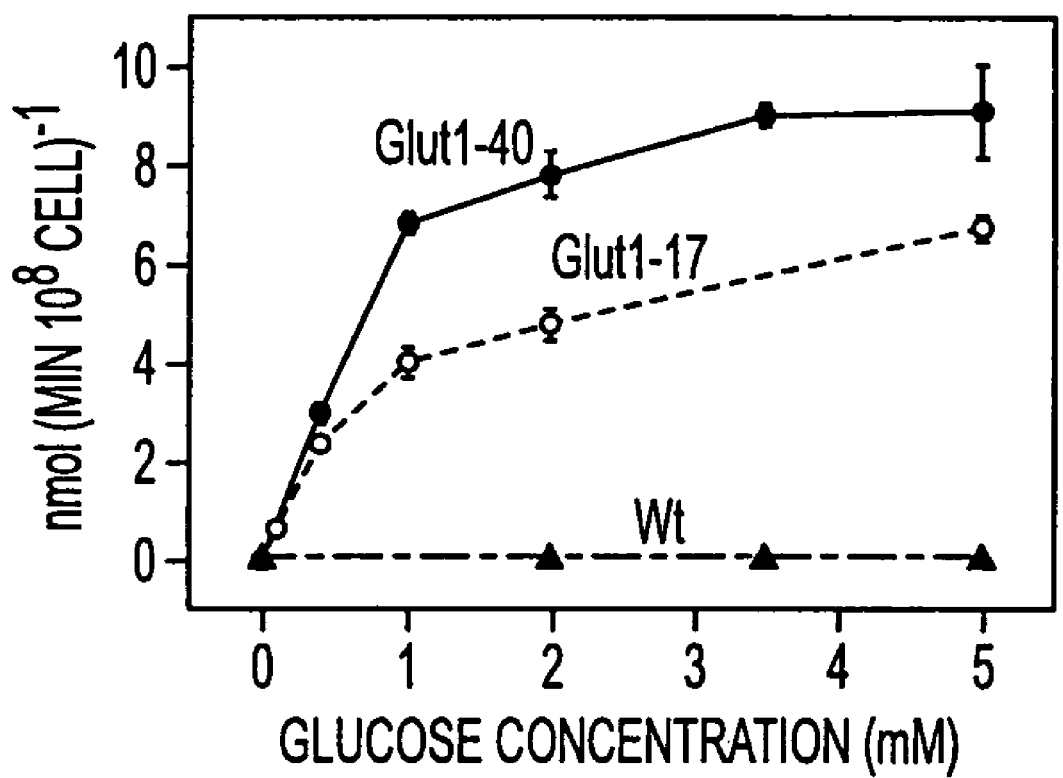
FIG. 5. Uptake of glucose by transformed and untransformed cell lines. Both Glut1GFP-40 and Glut1-17 were assayed for glucose uptake using the procedure described herein.
Figure 6A:
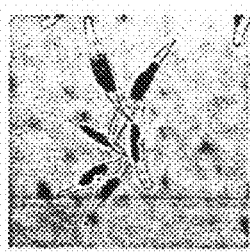
FIG. 6. Localization of Glut1 in *P. tricornutum* transformed with the chimeric gene encoding the Glut1-GFP fusion protein. The top panel shows a transmitted light image of untransformed *P. tricornutum* cells (A), fluorescence from the cells in the red channel (B), which represents chlorophyll fluorescence, and fluorescence from the cells in the green channel (C). The lower panel shows fluorescence in the green channel of cells that have been transformed with the GFP gene driven by an Fep promoter (D), and of cells that have been transformed with the chimeric Glut1-GFP gene (E, strain designated Glut1-40). All fluorescence images are single confocal optical sections. Scale bars=10 microns.
Figure 6B:
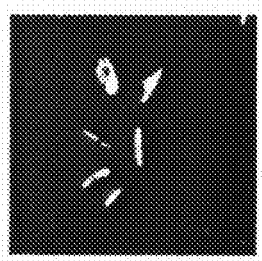
Figure 6C:
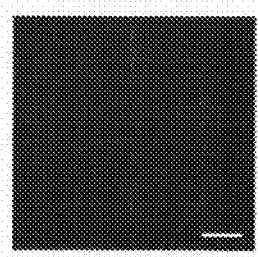
Figure 6D:
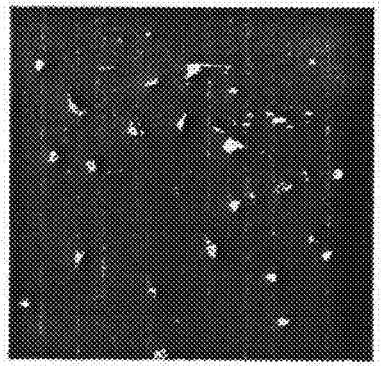
Figure 6E:
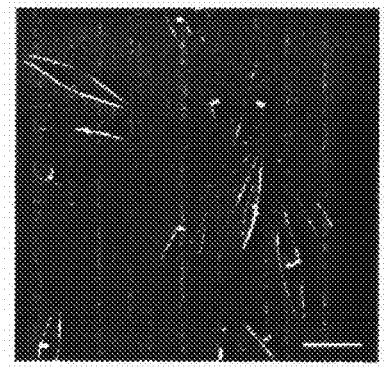

The Glut-13, Glut-17 and Glut GFP-40 transformants showed high rates of glucose uptake (FIG. 5). Transformant Glut-13 had a Km of 1.2 mM and a Vmax of 1.4-3 nmoles glucose ($10^8$ cells·min)$^{-1}$. Glut-17 had a Km of 0.9 mM and a Vmax of 1-5 nmoles glucose ($10^8$ cells·min)$^{-1}$. The Glut-17 transformant had a Km for glucose of 1.2 mM and a Vmax of 7.6 nmoles glucose ($10^8$ cells·min)$^{-1}$ while the Glut]GFP-40 transformant had a Km of approximately 1.0 mM and a Vmax of 13 nmoles glucose ($10^8$ cells·min)$^{-1}$. The Km values for glucose in the transformants are similar to those (1-2 mM) measured for human erythrocytes (Chisholm, S. W., (2000) *Nature*, 407:685; mueckler, et al., 1997). Differences in the Vmax probably reflect different levels of expression of the Glut1 gene, which would depend on the site of integration into the diatom genome. To further confirm that the glut1 transporter is functioning normally the specific inhibitor Cytochalasin B was incubated with the cell line Glut-13. Cytochalasin B is well known to be a specific inhibitor of type glucose transporters (Lu, et al., (1997) *J. Chromatog.*, 776: 81). In the presence of $5\times10^{-4}$ of Cytochalasin B glucose uptake was reduced to an undetectable level. The inhibitor data further support that the heterologous Glut1 transporter is functioning in the correct manner.

The glucose uptake kinetics for transformant Hup-2 was also measured in detail with a Km of 40 µM and a Vmax of 3 nmoles glucose ($10^8$ cells·min)$^{-1}$. The Km values are slightly higher than the published values measures for intact *Chlorella* cells and the Hup1 produced in yeast or *Xenopus*, which were 10-20 µM (Sauer N, Caspari T, Klebl F, Tanner W (1990) "Functional expression of the *Chlorella* hexose transporter in *Schzosaccharomyces pombe, Proc. Natl. Acad. Sci.* 87:7949-52; Aoshima H, Yamada M, Sauer N, Kornor E, Schobert C (1993) "Heterologous expression of the H+/hexose cotransporter from *Chlorella* in *Xenopus* oocytes and its characterization with respect to sugar specificity, pH and membrane potential," *J. Plant Physiol.* 141:293-297).

Example 8

Comparison of Light and Dark Growth for a Transformant

Growth of the Glut-17 transformant was measured in the light and dark in medium supplemented with glucose. Glucose levels were typically maintained between 5-10 g/L. Growth rates were monitored in cultures maintained in 50 mL of medium in 250 mL flasks with silicon foam closures. Samples were taken on a daily basis to measure cell numbers and nutrient levels. Flasks were shaken on a rotary platform at 100 rpm. High density cultures were grown in a 2 L Applikont fermentor using an agitation rate of 100 rpm, dissolved oxygen was maintained at >20% saturation and the pH was at 7.5.

Figure 7A:
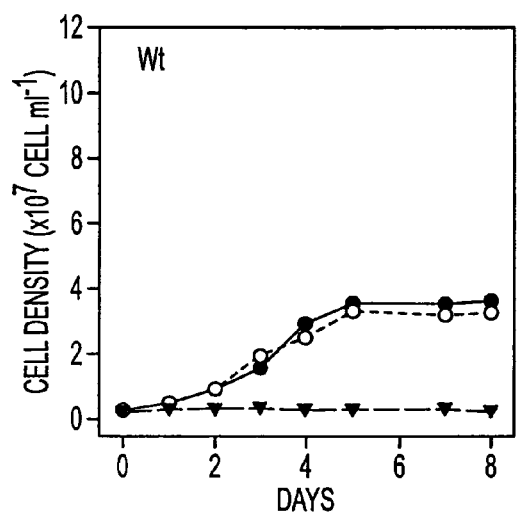
FIG. 7. Growth of wild-type cells and Glut1-17 under different conditions. The left panel shows the growth of wild type cells (Wt) and the right panel shows growth of Glut1-17 under various conditions. Cells were cultured in the light without supplemented glucose (closed circles), in the dark with supplemented glucose (closed triangles) or in the light with supplemented glucose (open circles).
Figure 7B:
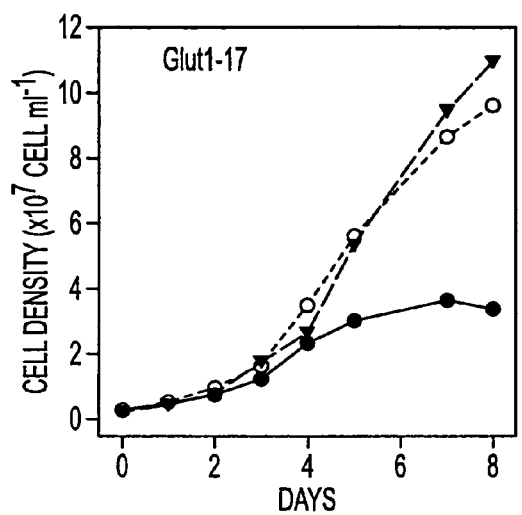

As shown in FIG. 7, both untransformed cells and the Glut-17 transformant grown in the light reached approximately the same cell densities ($2\times10^7$ cells·ml$^{-1}$). The addition of glucose to the medium did not change the growth characteristics of the untransformed strain. In contrast, the transformed strain attained a cell density that was approximately 5 times higher than that of the untransformed cells (over a five-day growth period). Furthermore, while untransformed cells are unable to grow in the dark in the presence of glucose, the Glut-17 transformant grows at the same rate and to the same cell density as when it is grown in the presence of glucose in the light. Strikingly, as the cultures become more dense and light absorption is attenuated by self-shading, the rate of growth of the transformant in the presence of glucose exceeds that of untransformed cells. If heterotrophic growth is conducted in a microbial fermentor with continuous addition of glucose and other nutrients to the medium, the density attained by cultures of the transformant can exceed that of wild-type cells by 10 to 20 fold, reaching densities of $5\times10^8$ cells·mL$^{-1}$.

Example 9

Mutated cells are produced by exposing cells to U.V. light (210-260 nm) at levels sufficient to result in >90% cell death.

Example 10

Mutated cells are produced by mixed cells in liquid with Nitrosoguanidine (a chemical mutagen) for 5 min at sufficient concentration to cause >90% cell death. The chemical mutagen is washed from the cells and the cells plated on solid media.

Example 11

The gene encoding the glucose transporter in a group of cells is inactivated by a gene replacement. A gene construct is produced containing the glucose transporter endogenous to the cells, with a the zeocin resistance cassette (described herein) inserted into the center of the transporter coding regions, resulting in a nonfunctional coding region of the glucose transporter. The gene construct is introduced into the cells using microparticle bombardment. This gene integrates and replaces the functional endogenous glucose transporter. Cells are grown on zeocin. Cells able to grow on zeocin are selected for further assays to determine whether the endogenous glucose transporter has been inactivated.

Example 12

Cells which have been mutagenized, as, for example, in Examples 9, 10, or 11, are grown in the presence of deoxyglucose. Cells which can grow are unable to take up the toxic deoxyglucose, which indicates that they do not possess functional glucose transporters. Cells without a functional glucose transporter are selected for further experiments.

A gene encoding a glucose transporter is inserted into the selected cells via the methods described herein. In conjunction with this transformation, the cells are also transformed with a second gene ("a gene of interest").

Cells are tested for their ability to grow on glucose in the dark, as described herein. Cells which can grow on glucose in the dark, indicating the expression of a functional glucose transporter, are selected for further-testing to determine whether they have also been transformed by the gene of interest.

The practice of the present invention employs, unless otherwise indicated, conventional molecular biology, microbiology, and recombinant DNA techniques within the skill of the art. Such techniques are well known to the skilled worker and are explained fully in the literature. See, e.g., Sambrook, J., Maniatis, T., & Fritsch, E. F. (1939), *Molecular Cloning: A Laboratory Manual*, 2$^{nd}$ ed., Cold Spring Harbor Press, Cold Spring Harbor, N.Y.; "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture".

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

For purposes of clarity of understanding, the foregoing invention h s been described in some detail by way of illustrations and examples in conjunction with specific embodiments, although other aspects, advantages and modifications will be apparent to those skilled in the art to which the invention pertains. The foregoing description and examples are intended to illustrate, but not limit the scope of the invention. Modifications of the above-described modes for carrying out the invention that are apparent to persons of skill in molecular biology, psychology, and/or related fields are intended to be within the scope of the invention, which is limited only by the appended claims.

All publications and patent applications mentioned in this specification are incorporated herein by reference to the same extent as if they had each been individually incorporated by reference. All publications and patent applications mentioned in this specification are indicative of the level of skill of those skilled in the art to which this invention pertains.

The invention claimed is:

1. A Bacillariophyta alga cell comprising an exogenous transgene, wherein the transgene comprises a nucleic acid construct encoding a glucose transporter selected from the group consisting of Glut1 (human erythrocyte glucose transporter 1) and Hup1 (Chlorella HUP1 Monosaccharide-H+ Symporter) under the control of a functionally linked promoter, wherein upon expression of the glucose transporter in an amount sufficient to transport glucose into the alga cell, said Bacillariophyta alga cell grows on glucose in the absence of light relative to the alga cell without the exogenous transgene.

2. The alga cell of claim 1, wherein the Bacillariophyta alga cell is selected from the group consisting of *Nitzschia, Navicula, Thalassiosira* and *Phaeodactylum*.

3. The alga cell of claim 2, wherein the *Phaeodactylum* cell is a *Phaeodactylum tricornutum*.

4. The alga cell of claim 1, wherein the promoter is a light harvesting promoter.

5. The alga cell of claim 4, wherein the light harvesting promoter is a fucoxanthin chlorophyll binding protein (fcp) promoter.

6. The alga cell of claim 5, wherein the fcp promoter is fcpA, fcpB, fcpC, or fcpE.

* * * * *

SEQUENCE LISTING

<160> NUMBER OF SEQ ID NOS: 8

<210> SEQ ID NO 1
<211> LENGTH: 28
<212> TYPE: DNA
<213> ORGANISM: Artificial Sequence
<220> FEATURE:
<223> OTHER INFORMATION: GLUTPHAT5' Primer

<400> SEQUENCE: 1
gactggatcc atggagccca gcagcaag                                    28

<210> SEQ ID NO 2
<211> LENGTH: 28
<212> TYPE: DNA
<213> ORGANISM: Artificial Sequence
<220> FEATURE:
<223> OTHER INFORMATION: GLUTPATT3' Primer -continued

<400> SEQUENCE: 2
gactaagctt tcacacttgg gaatcagc                               28

<210> SEQ ID NO 3
<211> LENGTH: 28
<212> TYPE: DNA
<213> ORGANISM: Artificial Sequence
<220> FEATURE:
<223> OTHER INFORMATION: HUPPHAT5'Primer

<400> SEQUENCE: 3
gatgaattca tggccggcgg tggtgtag                               28

<210> SEQ ID NO 4
<211> LENGTH: 29
<212> TYPE: DNA
<213> ORGANISM: Artificial Sequence
<220> FEATURE:
<223> OTHER INFORMATION: HUPPHAT3'Primer

<400> SEQUENCE: 4
gactaagctt ttacttcatc gcctttgac                              29

<210> SEQ ID NO 5
<211> LENGTH: 35
<212> TYPE: DNA
<213> ORGANISM: Artificial Sequence
<220> FEATURE:
<223> OTHER INFORMATION: HXT2PHAT5' Primer

<400> SEQUENCE: 5
gggaattcat tcaagatgtc tgagttcgct agaag                       35

<210> SEQ ID NO 6
<211> LENGTH: 29
<212> TYPE: DNA
<213> ORGANISM: Artificial Sequence
<220> FEATURE:
<223> OTHER INFORMATION: HXT2PHAT3'Primer

<400> SEQUENCE: 6
ccccgcatgc ttattcctcg gaaactctt                              29

<210> SEQ ID NO 7
<211> LENGTH: 29
<212> TYPE: DNA
<213> ORGANISM: Artificial Sequence
<220> FEATURE:
<223> OTHER INFORMATION: HXT4PHAT5' Primer

<400> SEQUENCE: 7
gggaatcatt caggatgtct gaagaagct                              29

<210> SEQ ID NO 8
<211> LENGTH: 27
<212> TYPE: DNA
<213> ORGANISM: Artificial Sequence
<220> FEATURE:
<223> OTHER INFORMATION: HXT4PHAT3'Primer

<400> SEQUENCE: 8
cctctagatt acttttttcc gaacatc                                27